US010405809B2

(12) United States Patent
Manicka et al.

(10) Patent No.: US 10,405,809 B2
(45) Date of Patent: *Sep. 10, 2019

(54) INJECTABLE DEVICE FOR PHYSIOLOGICAL MONITORING

(71) Applicant: MEDTRONIC MONITORING, INC., San Jose, CA (US)

(72) Inventors: Yatheendhar D. Manicka, Woodbury, MN (US); Badri Amurthur, Los Gatos, MN (US); Mark Bly, Falcon Heights, MN (US); Kristofer James, Eagan, MN (US); Imad Libbus, St. Paul, MN (US); Scott T. Mazar, Woodbury, MN (US); Jerry S. Wang, Edina, MN (US)

(73) Assignee: MEDTRONIC MONITORING, INC, San Jose, CA (US)

(*) Notice: Subject to any disclaimer, the term of this patent is extended or adjusted under 35 U.S.C. 154(b) by 1427 days.

This patent is subject to a terminal disclaimer.

(21) Appl. No.: 14/218,594

(22) Filed: Mar. 18, 2014

(65) Prior Publication Data

US 2014/0323821 A1  Oct. 30, 2014

Related U.S. Application Data

(63) Continuation of application No. 12/209,430, filed on Sep. 12, 2008, now Pat. No. 8,684,925.

(Continued)

(51) Int. Cl.
*A61B 5/07* (2006.01)
*A61B 5/053* (2006.01)
(Continued)

(52) U.S. Cl.
CPC .......... *A61B 5/7282* (2013.01); *A61B 5/0031* (2013.01); *A61B 5/0205* (2013.01);
(Continued)

(58) Field of Classification Search
CPC .......................... A61N 1/37205; A61B 5/1459
See application file for complete search history.

(56) References Cited

U.S. PATENT DOCUMENTS 834,261 A    10/1906 Chambers
2,087,124 A   7/1937 Smith et al.
(Continued)

FOREIGN PATENT DOCUMENTS

AU   2003-220574 A8   10/2003
EP       1487535 A2   12/2004
(Continued)

OTHER PUBLICATIONS

Abraham, "New approaches to monitoring heart failure before symptoms appear", Rev. Cardiovasc. Med., vol. 7 Suppl 1, 2006, pp. 33-41.

(Continued)

*Primary Examiner* — Scott T Luan
(74) *Attorney, Agent, or Firm* — Billion & Armitage; Michael A. Collins

(57) ABSTRACT

An injectable detecting device is provided for use in physiological monitoring. The device includes a plurality of sensors axially spaced along a body that provide an indication of at least one physiological event of a patient, a monitoring unit within the body coupled to the plurality of sensors configured to receive data from the plurality of sensors and create processed patient data, a power source within the body coupled to the monitoring unit, and a communication antenna external to the body coupled to the monitoring unit configured to transfer data to/from other devices.

17 Claims, 15 Drawing Sheets

Related U.S. Application Data

(60) Provisional application No. 61/055,666, filed on May 23, 2008, provisional application No. 60/972,537, filed on Sep. 14, 2007, provisional application No. 60/972,336, filed on Sep. 14, 2007, provisional application No. 60/972,329, filed on Sep. 14, 2007, provisional application No. 60/972,354, filed on Sep. 14, 2007.

(51) Int. Cl.
    *A61B 5/00*     (2006.01)
    *A61B 5/0205*     (2006.01)
    *A61B 5/145*     (2006.01)
    *A61B 5/042*     (2006.01)
    *A61N 1/372*     (2006.01)
    *A61B 5/11*     (2006.01)

(52) U.S. Cl.
CPC ........ *A61B 5/02055* (2013.01); *A61B 5/0422* (2013.01); *A61B 5/053* (2013.01); *A61B 5/07* (2013.01); *A61B 5/076* (2013.01); *A61B 5/14503* (2013.01); *A61B 5/4875* (2013.01); *A61B 5/686* (2013.01); *A61B 5/1118* (2013.01); *A61B 5/7232* (2013.01); *A61B 2560/0214* (2013.01); *A61B 2560/0468* (2013.01); *A61B 2562/0219* (2013.01); *A61B 2562/04* (2013.01); *A61B 2562/06* (2013.01); *A61B 2562/16* (2013.01); *A61N 1/37205* (2013.01)

(56) References Cited

U.S. PATENT DOCUMENTS

| | | |
|---|---|---|
| 2,184,511 A | 12/1939 | Bagno et al. |
| 3,170,459 A | 2/1965 | Phipps et al. |
| 3,232,291 A | 2/1966 | Parker |
| 3,370,459 A | 2/1968 | Cescati |
| 3,517,999 A | 6/1970 | Weaver |
| 3,620,216 A | 11/1971 | Szymanski |
| 3,677,260 A | 7/1972 | Funfstuck et al. |
| 3,805,769 A | 4/1974 | Sessions |
| 3,845,757 A | 11/1974 | Wyer |
| 3,874,368 A | 4/1975 | Asrican |
| 3,882,853 A | 5/1975 | Gofman et al. |
| 3,942,517 A | 3/1976 | Bowles et al. |
| 3,972,329 A | 8/1976 | Kaufman |
| 4,008,712 A | 2/1977 | Nyboer |
| 4,024,312 A | 5/1977 | Korpman |
| 4,077,406 A | 3/1978 | Sandhage et al. |
| 4,121,573 A | 10/1978 | Crovella et al. |
| 4,141,366 A | 2/1979 | Cross, Jr. et al. |
| RE30,101 E | 9/1979 | Kubicek et al. |
| 4,185,621 A | 1/1980 | Morrow |
| 4,216,462 A | 8/1980 | Digaicomo et al. |
| 4,300,575 A | 11/1981 | Wilson |
| 4,308,872 A | 1/1982 | Watson et al. |
| 4,358,678 A | 11/1982 | Lawrence |
| 4,409,983 A | 10/1983 | Albert |
| 4,450,527 A | 5/1984 | Sramek |
| 4,451,254 A | 5/1984 | Dinius et al. |
| 4,478,223 A | 10/1984 | Allor |
| 4,498,479 A | 2/1985 | Martio et al. |
| 4,522,211 A | 6/1985 | Bare et al. |
| 4,661,103 A | 4/1987 | Harman |
| 4,664,129 A | 5/1987 | Helzel et al. |
| 4,669,480 A | 6/1987 | Hoffman |
| 4,673,387 A | 6/1987 | Phillips et al. |
| 4,681,118 A | 7/1987 | Asai et al. |
| 4,692,685 A | 9/1987 | Blaze |
| 4,699,146 A | 10/1987 | Sieverding |
| 4,721,110 A | 1/1988 | Lampadius |
| 4,730,611 A | 3/1988 | Lamb |
| 4,733,107 A | 3/1988 | O'Shaughnessy et al. |
| 4,781,200 A | 11/1988 | Baker |
| 4,793,362 A | 12/1988 | Tedner |
| 4,838,273 A | 6/1989 | Cartmell |
| 4,838,279 A | 6/1989 | Fore |
| 4,850,370 A | 7/1989 | Dower |
| 4,880,004 A | 11/1989 | Baker, Jr. et al. |
| 4,895,163 A | 1/1990 | Libke et al. |
| 4,911,175 A | 3/1990 | Shizgal |
| 4,945,916 A | 8/1990 | Kretschmer et al. |
| 4,955,381 A | 9/1990 | Way et al. |
| 4,966,158 A | 10/1990 | Honma et al. |
| 4,981,139 A | 1/1991 | Pfohl |
| 4,988,335 A | 1/1991 | Prindle et al. |
| 4,989,612 A | 2/1991 | Fore |
| 5,001,632 A | 3/1991 | Hall-Tipping |
| 5,012,810 A | 5/1991 | Strand |
| 5,025,791 A | 6/1991 | Niwa |
| 5,027,824 A | 7/1991 | Dougherty et al. |
| 5,050,612 A | 9/1991 | Matsumura |
| 5,063,937 A | 11/1991 | Ezenwa et al. |
| 5,080,099 A | 1/1992 | Way et al. |
| 5,083,563 A | 1/1992 | Collins |
| 5,086,781 A | 2/1992 | Bookspan |
| 5,113,869 A | 5/1992 | Nappholz et al. |
| 5,125,412 A | 6/1992 | Thornton |
| 5,133,355 A | 7/1992 | Strand et al. |
| 5,140,985 A | 8/1992 | Schroeder et al. |
| 5,150,708 A | 9/1992 | Brooks |
| 5,168,874 A | 12/1992 | Segalowitz |
| 5,226,417 A | 7/1993 | Swedlow et al. |
| 5,241,300 A | 8/1993 | Buschmann |
| 5,257,627 A | 11/1993 | Rapoport |
| 5,271,411 A | 12/1993 | Ripley et al. |
| 5,273,532 A | 12/1993 | Niezink et al. |
| 5,282,840 A | 2/1994 | Hudrlik |
| 5,291,013 A | 3/1994 | Nafarrate et al. |
| 5,297,556 A | 3/1994 | Shankar |
| 5,301,677 A | 4/1994 | Hsung |
| 5,319,363 A | 6/1994 | Welch et al. |
| 5,331,966 A | 7/1994 | Bennett et al. |
| 5,335,664 A | 8/1994 | Nagashima |
| 5,343,869 A | 9/1994 | Pross et al. |
| 5,353,793 A | 10/1994 | Bornn |
| 5,362,069 A | 11/1994 | Hall-Tipping |
| 5,375,604 A | 12/1994 | Kelly et al. |
| 5,411,530 A | 5/1995 | Akhtar |
| 5,437,285 A | 8/1995 | Verrier et al. |
| 5,443,073 A | 8/1995 | Wang et al. |
| 5,449,000 A | 9/1995 | Libke et al. |
| 5,450,845 A | 9/1995 | Axel |
| 5,454,377 A | 10/1995 | Dzwonczyk et al. |
| 5,464,012 A | 11/1995 | Falcone |
| 5,469,859 A | 11/1995 | Tsoglin et al. |
| 5,482,036 A | 1/1996 | Diab et al. |
| 5,503,157 A | 4/1996 | Sramek |
| 5,511,548 A | 4/1996 | Riazzi |
| 5,511,553 A | 4/1996 | Segalowitz |
| 5,518,001 A | 5/1996 | Snell |
| 5,523,742 A | 6/1996 | Simkins et al. |
| 5,529,072 A | 6/1996 | Sramek |
| 5,544,661 A | 8/1996 | Davis et al. |
| 5,558,638 A | 9/1996 | Evers et al. |
| 5,560,368 A | 10/1996 | Berger |
| 5,564,429 A | 10/1996 | Bornn et al. |
| 5,564,434 A | 10/1996 | Halperin et al. |
| 5,566,671 A | 10/1996 | Lyons |
| 5,575,284 A | 11/1996 | Athan et al. |
| 5,607,454 A | 3/1997 | Cameron et al. |
| 5,632,272 A | 5/1997 | Diab et al. |
| 5,634,468 A | 6/1997 | Platt et al. |
| 5,642,734 A | 7/1997 | Ruben et al. |
| 5,673,704 A | 10/1997 | Marchlinski et al. |
| 5,678,562 A | 10/1997 | Sellers |
| 5,687,717 A | 11/1997 | Halpern et al. |
| 5,718,234 A | 2/1998 | Warden et al. |
| 5,724,025 A | 3/1998 | Tavori |
| 5,738,107 A | 4/1998 | Martinsen et al. |
| 5,748,103 A | 5/1998 | Flach et al. |

(56) References Cited

U.S. PATENT DOCUMENTS

| | | |
|---|---|---|
| 5,767,791 A | 6/1998 | Stoop et al. |
| 5,769,793 A | 6/1998 | Pincus et al. |
| 5,772,508 A | 6/1998 | Sugita et al. |
| 5,772,586 A | 6/1998 | Heinonen et al. |
| 5,778,882 A | 7/1998 | Raymond et al. |
| 5,788,643 A | 8/1998 | Feldman |
| 5,803,915 A | 9/1998 | Kremenchugsky et al. |
| 5,807,272 A | 9/1998 | Kun et al. |
| 5,814,079 A | 9/1998 | Kieval |
| 5,817,035 A | 10/1998 | Sullivan |
| 5,833,603 A | 11/1998 | Kovacs et al. |
| 5,836,990 A | 11/1998 | Li |
| 5,855,614 A | 1/1999 | Stevens et al. |
| 5,860,860 A | 1/1999 | Clayman |
| 5,862,802 A | 1/1999 | Bird |
| 5,862,803 A | 1/1999 | Besson et al. |
| 5,865,733 A | 2/1999 | Malinouskas et al. |
| 5,876,353 A | 3/1999 | Riff |
| 5,904,708 A | 5/1999 | Goedeke |
| 5,935,079 A | 8/1999 | Swanson et al. |
| 5,941,831 A | 8/1999 | Turcott |
| 5,944,659 A | 8/1999 | Flach et al. |
| 5,949,636 A | 9/1999 | Johnson et al. |
| 5,957,854 A | 9/1999 | Besson et al. |
| 5,957,861 A | 9/1999 | Combs et al. |
| 5,964,703 A | 10/1999 | Goodman et al. |
| 5,970,986 A | 10/1999 | Bolz et al. |
| 5,984,102 A | 11/1999 | Tay |
| 5,987,352 A | 11/1999 | Klein et al. |
| 6,007,532 A | 12/1999 | Netherly |
| 6,027,523 A | 2/2000 | Schmieding |
| 6,045,513 A | 4/2000 | Stone et al. |
| 6,047,203 A | 4/2000 | Sackner et al. |
| 6,047,259 A | 4/2000 | Campbell et al. |
| 6,049,730 A | 4/2000 | Kristbjamarson |
| 6,050,267 A | 4/2000 | Nardella et al. |
| 6,050,951 A | 4/2000 | Friedman et al. |
| 6,052,615 A | 4/2000 | Feild et al. |
| 6,067,467 A | 5/2000 | John |
| 6,080,106 A | 6/2000 | Lloyd et al. |
| 6,081,735 A | 6/2000 | Diab et al. |
| 6,095,991 A | 8/2000 | Krausman et al. |
| 6,102,856 A | 8/2000 | Groff et al. |
| 6,104,949 A | 8/2000 | Pitts et al. |
| 6,112,224 A | 8/2000 | Peifer et al. |
| 6,117,077 A | 9/2000 | Del Mar et al. |
| 6,125,297 A | 9/2000 | Siconolfi |
| 6,129,744 A | 10/2000 | Boute et al. |
| 6,141,575 A | 10/2000 | Price |
| 6,144,878 A | 11/2000 | Schroeppel et al. |
| 6,164,284 A | 12/2000 | Schulman et al. |
| 6,181,963 B1 | 1/2001 | Chin et al. |
| 6,185,452 B1 | 2/2001 | Schulman et al. |
| 6,190,313 B1 | 2/2001 | Hinkle |
| 6,190,324 B1 | 2/2001 | Kieval et al. |
| 6,198,394 B1 | 3/2001 | Jacobsen et al. |
| 6,198,955 B1 | 3/2001 | Axelgaard et al. |
| 6,208,894 B1 | 3/2001 | Schulman et al. |
| 6,212,427 B1 | 4/2001 | Hoover |
| 6,213,942 B1 | 4/2001 | Flach et al. |
| 6,225,901 B1 | 5/2001 | Kail, IV |
| 6,245,021 B1 | 6/2001 | Stampfer |
| 6,259,939 B1 | 7/2001 | Rogel |
| 6,272,377 B1 | 8/2001 | Sweeney et al. |
| 6,277,078 B1 | 8/2001 | Porat et al. |
| 6,287,252 B1 | 9/2001 | Lugo |
| 6,289,238 B1 | 9/2001 | Besson et al. |
| 6,290,646 B1 | 9/2001 | Cosentino et al. |
| 6,295,466 B1 | 9/2001 | Ishikawa et al. |
| 6,305,943 B1 | 10/2001 | Pougatchev et al. |
| 6,306,088 B1 | 10/2001 | Krausman et al. |
| 6,308,094 B1 | 10/2001 | Krausman et al. |
| 6,312,378 B1 | 11/2001 | Bardy |
| 6,315,721 B2 | 11/2001 | Schulman et al. |
| 6,327,487 B1 | 12/2001 | Stratbucker |
| 6,330,464 B1 | 12/2001 | Colvin, Jr. et al. |
| 6,336,903 B1 | 1/2002 | Bardy |
| 6,339,722 B1 | 1/2002 | Heethaar et al. |
| 6,343,140 B1 | 1/2002 | Brooks |
| 6,347,245 B1 | 2/2002 | Lee et al. |
| 6,358,208 B1 | 3/2002 | Lang et al. |
| 6,385,473 B1 | 5/2002 | Haines et al. |
| 6,398,727 B1 | 6/2002 | Bui et al. |
| 6,400,982 B2 | 6/2002 | Sweeney et al. |
| 6,409,674 B1 | 6/2002 | Brockway et al. |
| 6,411,853 B1 | 6/2002 | Millot et al. |
| 6,416,471 B1 | 7/2002 | Kumar et al. |
| 6,440,069 B1 | 8/2002 | Raymond |
| 6,442,422 B1 | 8/2002 | Duckert |
| 6,450,820 B1 | 9/2002 | Palsson et al. |
| 6,450,953 B1 | 9/2002 | Place et al. |
| 6,454,707 B1 | 9/2002 | Casscells, III et al. |
| 6,454,708 B1 | 9/2002 | Ferguson et al. |
| 6,459,930 B1 | 10/2002 | Takehara et al. |
| 6,463,328 B1 | 10/2002 | John |
| 6,473,640 B1 | 10/2002 | Erlebacher |
| 6,480,733 B1 | 11/2002 | Turcott |
| 6,480,734 B1 | 11/2002 | Zhang et al. |
| 6,490,478 B1 | 12/2002 | Zhang et al. |
| 6,491,647 B1 | 12/2002 | Bridger et al. |
| 6,494,829 B1 | 12/2002 | New, Jr. et al. |
| 6,496,715 B1 | 12/2002 | Lee et al. |
| 6,512,949 B1 | 1/2003 | Combs et al. |
| 6,520,967 B1 | 2/2003 | Cauthen |
| 6,527,711 B1 | 3/2003 | Stivoric et al. |
| 6,527,729 B1 | 3/2003 | Turcott |
| 6,544,173 B2 | 4/2003 | West et al. |
| 6,544,174 B2 | 4/2003 | West et al. |
| 6,551,251 B2 | 4/2003 | Zuckerwar et al. |
| 6,551,252 B2 | 4/2003 | Sackner et al. |
| 6,569,160 B1 | 5/2003 | Goldin et al. |
| 6,572,557 B2 | 6/2003 | Tchou et al. |
| 6,572,636 B1 | 6/2003 | Hagen et al. |
| 6,577,139 B2 | 6/2003 | Cooper |
| 6,577,893 B1 | 6/2003 | Besson et al. |
| 6,577,897 B1 | 6/2003 | Shurubura et al. |
| 6,579,231 B1 | 6/2003 | Phipps |
| 6,580,942 B1 | 6/2003 | Wiltshire |
| 6,584,343 B1 | 6/2003 | Ransbury et al. |
| 6,587,715 B2 | 7/2003 | Singer |
| 6,589,170 B1 | 7/2003 | Flach et al. |
| 6,595,927 B2 | 7/2003 | Pitts-Crick et al. |
| 6,595,929 B2 | 7/2003 | Stivoric et al. |
| 6,600,949 B1 | 7/2003 | Turcott |
| 6,602,201 B1 | 8/2003 | Hepp et al. |
| 6,605,038 B1 | 8/2003 | Teller et al. |
| 6,611,705 B2 | 8/2003 | Hopman et al. |
| 6,616,606 B1 | 9/2003 | Petersen et al. |
| 6,622,042 B1 | 9/2003 | Thacker |
| 6,636,754 B1 | 10/2003 | Baura et al. |
| 6,641,542 B2 | 11/2003 | Cho et al. |
| 6,645,153 B2 | 11/2003 | Kroll et al. |
| 6,649,829 B2 | 11/2003 | Garber et al. |
| 6,650,917 B2 | 11/2003 | Diab et al. |
| 6,658,300 B2 | 12/2003 | Govari et al. |
| 6,659,947 B1 | 12/2003 | Carter et al. |
| 6,659,949 B1 | 12/2003 | Lang et al. |
| 6,687,540 B2 | 2/2004 | Marcovecchio |
| 6,697,658 B2 | 2/2004 | Al-Ali |
| RE38,476 E | 3/2004 | Diab et al. |
| 6,699,200 B2 | 3/2004 | Cao et al. |
| 6,701,271 B2 | 3/2004 | Willner et al. |
| 6,711,423 B2 | 3/2004 | Colvin, Jr. |
| 6,714,813 B2 | 3/2004 | Ishigooka et al. |
| RE38,492 E | 4/2004 | Diab et al. |
| 6,721,594 B2 | 4/2004 | Conley et al. |
| 6,728,572 B2 | 4/2004 | Hsu et al. |
| 6,748,269 B2 | 6/2004 | Thompson et al. |
| 6,749,566 B2 | 6/2004 | Russ |
| 6,751,498 B1 | 6/2004 | Greenberg et al. |
| 6,760,617 B2 | 7/2004 | Ward |
| 6,773,396 B2 | 8/2004 | Flach et al. |
| 6,775,566 B2 | 8/2004 | Nissila |
| 6,790,178 B1 | 9/2004 | Mault et al. |

(56) References Cited

U.S. PATENT DOCUMENTS

| | | |
|---|---|---|
| 6,795,722 B2 | 9/2004 | Sheraton et al. |
| 6,814,706 B2 | 11/2004 | Barton et al. |
| 6,816,744 B2 | 11/2004 | Garfield et al. |
| 6,821,249 B2 | 11/2004 | Casscells et al. |
| 6,824,515 B2 | 11/2004 | Suorsa et al. |
| 6,827,690 B2 | 12/2004 | Bardy |
| 6,829,503 B2 | 12/2004 | Alt |
| 6,858,006 B2 | 2/2005 | MacCarter et al. |
| 6,871,211 B2 | 3/2005 | Labounty et al. |
| 6,878,121 B2 | 4/2005 | Krausman et al. |
| 6,879,850 B2 | 4/2005 | Kimball |
| 6,881,191 B2 | 4/2005 | Oakley et al. |
| 6,887,201 B2 | 5/2005 | Bardy |
| 6,890,096 B2 | 5/2005 | Tokita et al. |
| 6,893,396 B2 | 5/2005 | Schulze et al. |
| 6,894,204 B2 | 5/2005 | Dunshee |
| 6,906,530 B2 | 6/2005 | Geisel |
| 6,912,414 B2 | 6/2005 | Tong |
| 6,936,006 B2 | 8/2005 | Sarbra |
| 6,940,403 B2 | 9/2005 | Kail |
| 6,942,622 B1 | 9/2005 | Turcott |
| 6,952,695 B1 | 10/2005 | Trinks et al. |
| 6,970,742 B2 | 11/2005 | Mann et al. |
| 6,972,683 B2 | 12/2005 | Lestienne et al. |
| 6,978,177 B1 | 12/2005 | Chen et al. |
| 6,980,851 B2 | 12/2005 | Zhu et al. |
| 6,980,852 B2 | 12/2005 | Jersey-Willuhn et al. |
| 6,985,078 B2 | 1/2006 | Suzuki et al. |
| 6,987,965 B2 | 1/2006 | Ng et al. |
| 6,988,989 B2 | 1/2006 | Weiner et al. |
| 6,993,378 B2 | 1/2006 | Wiederhold et al. |
| 6,997,879 B1 | 2/2006 | Turcott |
| 7,003,346 B2 | 2/2006 | Singer |
| 7,009,362 B2 | 3/2006 | Tsukamoto et al. |
| 7,010,340 B2 | 3/2006 | Scarantino et al. |
| 7,018,338 B2 | 3/2006 | Vetter et al. |
| 7,020,508 B2 | 3/2006 | Stivoric et al. |
| 7,027,862 B2 | 4/2006 | Dahl et al. |
| 7,041,062 B2 | 5/2006 | Friedrichs et al. |
| 7,044,911 B2 | 5/2006 | Drinan et al. |
| 7,047,067 B2 | 5/2006 | Gray et al. |
| 7,050,846 B2 | 5/2006 | Sweeney et al. |
| 7,054,679 B2 | 5/2006 | Hirsh |
| 7,059,767 B2 | 6/2006 | Tokita et al. |
| 7,088,242 B2 | 8/2006 | Aupperle et al. |
| 7,113,826 B2 | 9/2006 | Henry et al. |
| 7,118,531 B2 | 10/2006 | Krill |
| 7,127,370 B2 | 10/2006 | Kelly et al. |
| 7,129,836 B2 | 10/2006 | Lawson et al. |
| 7,130,396 B2 | 10/2006 | Rogers et al. |
| 7,130,679 B2 | 10/2006 | Parsonnet et al. |
| 7,133,716 B2 | 11/2006 | Kraemer et al. |
| 7,136,697 B2 | 11/2006 | Singer |
| 7,136,703 B1 | 11/2006 | Cappa et al. |
| 7,142,907 B2 | 11/2006 | Xue et al. |
| 7,149,574 B2 | 12/2006 | Yun et al. |
| 7,149,773 B2 | 12/2006 | Haller et al. |
| 7,153,262 B2 | 12/2006 | Stivoric et al. |
| 7,156,807 B2 | 1/2007 | Carter et al. |
| 7,156,808 B2 | 1/2007 | Quy et al. |
| 7,160,252 B2 | 1/2007 | Cho et al. |
| 7,160,253 B2 | 1/2007 | Nissila et al. |
| 7,166,063 B2 | 1/2007 | Rahman et al. |
| 7,167,743 B2 | 1/2007 | Heruth et al. |
| 7,184,821 B2 | 2/2007 | Belalcazar et al. |
| 7,191,000 B2 | 3/2007 | Zhu et al. |
| 7,194,306 B1 | 3/2007 | Turcott |
| 7,206,630 B1 | 4/2007 | Tarter |
| 7,212,849 B2 | 5/2007 | Zhang et al. |
| 7,215,984 B2 | 5/2007 | Doab et al. |
| 7,215,991 B2 | 5/2007 | Besson et al. |
| 7,238,159 B2 | 7/2007 | Banet et al. |
| 7,248,916 B2 | 7/2007 | Bardy |
| 7,251,524 B1 | 7/2007 | Hepp et al. |
| 7,257,438 B2 | 8/2007 | Kinast |
| 7,261,690 B2 | 8/2007 | Teller et al. |
| 7,277,741 B2 | 10/2007 | Debreczeny et al. |
| 7,284,904 B2 | 10/2007 | Tokita et al. |
| 7,285,090 B2 | 10/2007 | Stivoric et al. |
| 7,294,105 B1 | 11/2007 | Islam |
| 7,295,879 B2 | 11/2007 | Denker et al. |
| 7,297,119 B2 | 11/2007 | Westbrook et al. |
| 7,318,808 B2 | 1/2008 | Tarassenko et al. |
| 7,319,386 B2 | 1/2008 | Collins et al. |
| 7,336,187 B2 | 2/2008 | Hubbard, Jr. et al. |
| 7,346,380 B2 | 3/2008 | Axelgaard et al. |
| 7,382,247 B2 | 6/2008 | Welch et al. |
| 7,384,398 B2 | 6/2008 | Gagnadre et al. |
| 7,390,299 B2 | 6/2008 | Weiner et al. |
| 7,395,106 B2 | 7/2008 | Ryu et al. |
| 7,423,526 B2 | 9/2008 | Despotis |
| 7,423,537 B2 | 9/2008 | Bonnet et al. |
| 7,443,302 B2 | 10/2008 | Reeder et al. |
| 7,450,024 B2 | 11/2008 | Wildman et al. |
| 7,468,032 B2 | 12/2008 | Stahmann et al. |
| 7,510,699 B2 | 3/2009 | Black et al. |
| 7,701,227 B2 | 4/2010 | Saulnier et al. |
| 7,813,778 B2 | 10/2010 | Benaron et al. |
| 7,881,763 B2 | 2/2011 | Brauker et al. |
| 7,942,824 B1 | 5/2011 | Kayyali et al. |
| 8,160,680 B2 | 4/2012 | Boyden et al. |
| 2001/0047127 A1 | 11/2001 | New, Jr. et al. |
| 2002/0019586 A1 | 2/2002 | Teller et al. |
| 2002/0019588 A1 | 2/2002 | Marro et al. |
| 2002/0022786 A1 | 2/2002 | Takehara et al. |
| 2002/0028989 A1 | 3/2002 | Pelletier et al. |
| 2002/0032581 A1 | 3/2002 | Reitberg |
| 2002/0045836 A1 | 4/2002 | Alkawwas et al. |
| 2002/0088465 A1 | 7/2002 | Hill |
| 2002/0099277 A1 | 7/2002 | Harry et al. |
| 2002/0116009 A1 | 8/2002 | Fraser et al. |
| 2002/0123672 A1 | 9/2002 | Christophersom et al. |
| 2002/0123674 A1 | 9/2002 | Plicchi et al. |
| 2002/0138017 A1 | 9/2002 | Bui et al. |
| 2002/0167389 A1 | 11/2002 | Uchikoba et al. |
| 2003/0009092 A1 | 1/2003 | Parker |
| 2003/0023184 A1 | 1/2003 | Pitts-Crick et al. |
| 2003/0028221 A1 | 2/2003 | Zhu et al. |
| 2003/0028321 A1 | 2/2003 | Brunner et al. |
| 2003/0051144 A1 | 3/2003 | Williams |
| 2003/0055460 A1 | 3/2003 | Owen et al. |
| 2003/0083581 A1 | 5/2003 | Taha et al. |
| 2003/0085717 A1 | 5/2003 | Cooper |
| 2003/0087244 A1 | 5/2003 | McCarthy |
| 2003/0092975 A1 | 5/2003 | Casscells, III et al. |
| 2003/0093125 A1 | 5/2003 | Zhu et al. |
| 2003/0093298 A1 | 5/2003 | Hernandez et al. |
| 2003/0100367 A1 | 5/2003 | Cooke |
| 2003/0105411 A1 | 6/2003 | Smallwood et al. |
| 2003/0135127 A1 | 7/2003 | Sackner et al. |
| 2003/0143544 A1 | 7/2003 | McCarthy |
| 2003/0149349 A1 | 8/2003 | Jensen |
| 2003/0187370 A1 | 10/2003 | Kodama |
| 2003/0191503 A1 | 10/2003 | Zhu et al. |
| 2003/0212319 A1 | 11/2003 | Magill |
| 2003/0221687 A1 | 12/2003 | Kaigler |
| 2003/0233129 A1 | 12/2003 | Matos |
| 2004/0006279 A1 | 1/2004 | Arad (Abboud) |
| 2004/0010303 A1 | 1/2004 | Bolea et al. |
| 2004/0015058 A1 | 1/2004 | Besson et al. |
| 2004/0019292 A1 | 1/2004 | Drinan et al. |
| 2004/0044293 A1 | 3/2004 | Burton |
| 2004/0049132 A1 | 3/2004 | Barron et al. |
| 2004/0064133 A1 | 4/2004 | Miller et al. |
| 2004/0068204 A1 | 4/2004 | Imran et al. |
| 2004/0073094 A1 | 4/2004 | Baker |
| 2004/0073126 A1 | 4/2004 | Rowlandson |
| 2004/0077954 A1 | 4/2004 | Oakley et al. |
| 2004/0100376 A1 | 5/2004 | Lye et al. |
| 2004/0102683 A1 | 5/2004 | Khanuja et al. |
| 2004/0106951 A1 | 6/2004 | Edman et al. |
| 2004/0122489 A1 | 6/2004 | Mazar et al. |
| 2004/0127790 A1 | 7/2004 | Lang et al. |
| 2004/0133079 A1 | 7/2004 | Mazar et al. |

(56) References Cited

U.S. PATENT DOCUMENTS

| | | |
|---|---|---|
| 2004/0133081 A1 | 7/2004 | Teller et al. |
| 2004/0134496 A1 | 7/2004 | Cho et al. |
| 2004/0143170 A1 | 7/2004 | DuRousseau |
| 2004/0147969 A1 | 7/2004 | Mann et al. |
| 2004/0152956 A1 | 8/2004 | Korman |
| 2004/0158132 A1 | 8/2004 | Zaleski |
| 2004/0167389 A1 | 8/2004 | Brabrand |
| 2004/0172080 A1 | 9/2004 | Stadler et al. |
| 2004/0199056 A1 | 10/2004 | Husemann et al. |
| 2004/0215240 A1 | 10/2004 | Lovett et al. |
| 2004/0215247 A1 | 10/2004 | Bolz |
| 2004/0220639 A1 | 11/2004 | Mulligan et al. |
| 2004/0225199 A1 | 11/2004 | Evanyk et al. |
| 2004/0225203 A1 | 11/2004 | Jemison et al. |
| 2004/0243018 A1 | 12/2004 | Organ et al. |
| 2004/0267142 A1 | 12/2004 | Paul |
| 2005/0015094 A1 | 1/2005 | Keller |
| 2005/0015095 A1 | 1/2005 | Keller |
| 2005/0020935 A1 | 1/2005 | Helzel et al. |
| 2005/0027175 A1 | 2/2005 | Yang |
| 2005/0027204 A1 | 2/2005 | Kligfield et al. |
| 2005/0027207 A1 | 2/2005 | Westbrook et al. |
| 2005/0027918 A1 | 2/2005 | Govindarajulu et al. |
| 2005/0043675 A1 | 2/2005 | Pastore et al. |
| 2005/0054944 A1 | 3/2005 | Nakada et al. |
| 2005/0059867 A1 | 3/2005 | Chung |
| 2005/0065445 A1 | 3/2005 | Arzbaecher et al. |
| 2005/0065571 A1 | 3/2005 | Imran |
| 2005/0070768 A1 | 3/2005 | Zhu et al. |
| 2005/0070778 A1 | 3/2005 | Lackey et al. |
| 2005/0079132 A1 | 4/2005 | Wang et al. |
| 2005/0080346 A1 | 4/2005 | Gianchandani et al. |
| 2005/0080460 A1 | 4/2005 | Wang et al. |
| 2005/0080463 A1 | 4/2005 | Stahmann et al. |
| 2005/0085734 A1 | 4/2005 | Tehrani |
| 2005/0091338 A1 | 4/2005 | de la Huerga |
| 2005/0096513 A1 | 5/2005 | Ozguz et al. |
| 2005/0107870 A1 | 5/2005 | Wang et al. |
| 2005/0113703 A1 | 5/2005 | Farringdon et al. |
| 2005/0124878 A1 | 6/2005 | Sharony |
| 2005/0124901 A1 | 6/2005 | Misczynski et al. |
| 2005/0124908 A1 | 6/2005 | Belalcazar et al. |
| 2005/0131288 A1 | 6/2005 | Turner et al. |
| 2005/0137464 A1 | 6/2005 | Bomba |
| 2005/0137626 A1 | 6/2005 | Pastore et al. |
| 2005/0148895 A1 | 7/2005 | Misczynski et al. |
| 2005/0158539 A1 | 7/2005 | Murphy et al. |
| 2005/0177038 A1 | 8/2005 | Kolpin et al. |
| 2005/0187482 A1 | 8/2005 | O'Brien et al. |
| 2005/0187796 A1 | 8/2005 | Rosenfeld et al. |
| 2005/0192488 A1 | 9/2005 | Bryenton et al. |
| 2005/0197654 A1 | 9/2005 | Edman et al. |
| 2005/0203433 A1 | 9/2005 | Singer |
| 2005/0203435 A1 | 9/2005 | Nakada |
| 2005/0203436 A1 | 9/2005 | Davies |
| 2005/0203637 A1 | 9/2005 | Edman et al. |
| 2005/0206518 A1 | 9/2005 | Welch et al. |
| 2005/0215914 A1 | 9/2005 | Bornzin et al. |
| 2005/0215918 A1 | 9/2005 | Frantz et al. |
| 2005/0228234 A1 | 10/2005 | Yang |
| 2005/0228238 A1 | 10/2005 | Monitzer |
| 2005/0228244 A1 | 10/2005 | Banet |
| 2005/0239493 A1 | 10/2005 | Batkin et al. |
| 2005/0240087 A1 | 10/2005 | Keenan et al. |
| 2005/0251044 A1 | 11/2005 | Hoctor et al. |
| 2005/0256418 A1 | 11/2005 | Mietus et al. |
| 2005/0261598 A1 | 11/2005 | Banet et al. |
| 2005/0261743 A1 | 11/2005 | Kroll |
| 2005/0267376 A1 | 12/2005 | Marossero et al. |
| 2005/0267377 A1 | 12/2005 | Marossero et al. |
| 2005/0267381 A1 | 12/2005 | Benditt et al. |
| 2005/0273023 A1 | 12/2005 | Bystrom et al. |
| 2005/0277841 A1 | 12/2005 | Shennib |
| 2005/0277842 A1 | 12/2005 | Silva |
| 2005/0277992 A1 | 12/2005 | Koh et al. |
| 2005/0280531 A1 | 12/2005 | Fadem et al. |
| 2005/0283197 A1 | 12/2005 | Daum et al. |
| 2005/0288601 A1 | 12/2005 | Wood et al. |
| 2006/0004300 A1 | 1/2006 | Kennedy |
| 2006/0004377 A1 | 1/2006 | Keller |
| 2006/0009697 A1 | 1/2006 | Banet et al. |
| 2006/0009701 A1 | 1/2006 | Nissila et al. |
| 2006/0010090 A1 | 1/2006 | Brockway et al. |
| 2006/0020218 A1 | 1/2006 | Freeman et al. |
| 2006/0025661 A1 | 2/2006 | Sweeney et al. |
| 2006/0030781 A1 | 2/2006 | Shennib |
| 2006/0030782 A1 | 2/2006 | Shennib |
| 2006/0031102 A1 | 2/2006 | Teller et al. |
| 2006/0041280 A1 | 2/2006 | Stahmann et al. |
| 2006/0047215 A1 | 3/2006 | Newman et al. |
| 2006/0052678 A1 | 3/2006 | Drinan et al. |
| 2006/0058543 A1 | 3/2006 | Walter et al. |
| 2006/0058593 A1 | 3/2006 | Drinan et al. |
| 2006/0064030 A1 | 3/2006 | Cosentino et al. |
| 2006/0064040 A1 | 3/2006 | Berger et al. |
| 2006/0064142 A1 | 3/2006 | Chavan et al. |
| 2006/0066449 A1 | 3/2006 | Johnson |
| 2006/0074283 A1 | 4/2006 | Henderson et al. |
| 2006/0074462 A1 | 4/2006 | Verhoef |
| 2006/0075257 A1 | 4/2006 | Martis et al. |
| 2006/0084881 A1 | 4/2006 | Korzinov et al. |
| 2006/0085049 A1 | 4/2006 | Cory et al. |
| 2006/0089679 A1 | 4/2006 | Zhu et al. |
| 2006/0094948 A1 | 5/2006 | Gough et al. |
| 2006/0102476 A1 | 5/2006 | Niwa et al. |
| 2006/0116592 A1 | 6/2006 | Zhou et al. |
| 2006/0122474 A1 | 6/2006 | Teller et al. |
| 2006/0135858 A1 | 6/2006 | Nidd et al. |
| 2006/0142654 A1 | 6/2006 | Rytky |
| 2006/0142820 A1 | 6/2006 | Von Arx et al. |
| 2006/0149168 A1 | 7/2006 | Czarnek |
| 2006/0155174 A1 | 7/2006 | Glukhovsky et al. |
| 2006/0155183 A1 | 7/2006 | Kroecker et al. |
| 2006/0155200 A1 | 7/2006 | Ng |
| 2006/0161073 A1 | 7/2006 | Singer |
| 2006/0161205 A1 | 7/2006 | Mitrani et al. |
| 2006/0161459 A9 | 7/2006 | Rosenfeld et al. |
| 2006/0173257 A1 | 8/2006 | Nagai et al. |
| 2006/0173269 A1 | 8/2006 | Glossop |
| 2006/0195020 A1 | 8/2006 | Martin et al. |
| 2006/0195039 A1 | 8/2006 | Drew et al. |
| 2006/0195097 A1 | 8/2006 | Evans et al. |
| 2006/0195144 A1 | 8/2006 | Giftakis et al. |
| 2006/0202816 A1 | 9/2006 | Crump et al. |
| 2006/0212097 A1 | 9/2006 | Varadan et al. |
| 2006/0224051 A1 | 10/2006 | Teller et al. |
| 2006/0224072 A1 | 10/2006 | Shennib |
| 2006/0224079 A1 | 10/2006 | Washchuk |
| 2006/0235281 A1 | 10/2006 | Tuccillo |
| 2006/0235316 A1 | 10/2006 | Ungless et al. |
| 2006/0235489 A1 | 10/2006 | Drew et al. |
| 2006/0241641 A1 | 10/2006 | Albans et al. |
| 2006/0241701 A1 | 10/2006 | Markowitz et al. |
| 2006/0241722 A1 | 10/2006 | Thacker et al. |
| 2006/0247545 A1 | 11/2006 | St Martin |
| 2006/0252999 A1 | 11/2006 | Devaul et al. |
| 2006/0253005 A1 | 11/2006 | Drinan et al. |
| 2006/0253044 A1 | 11/2006 | Zhang et al. |
| 2006/0258952 A1 | 11/2006 | Stahmann et al. |
| 2006/0264730 A1 | 11/2006 | Stivoric et al. |
| 2006/0264767 A1 | 11/2006 | Shennib |
| 2006/0264776 A1 | 11/2006 | Stahmann et al. |
| 2006/0271116 A1 | 11/2006 | Stahmann et al. |
| 2006/0276714 A1 | 12/2006 | Holt et al. |
| 2006/0281981 A1 | 12/2006 | Jang et al. |
| 2006/0281996 A1 | 12/2006 | Kuo et al. |
| 2006/0293571 A1 | 12/2006 | Bao et al. |
| 2006/0293609 A1 | 12/2006 | Stahmann et al. |
| 2007/0010702 A1 | 1/2007 | Wang et al. |
| 2007/0010721 A1 | 1/2007 | Chen et al. |
| 2007/0010750 A1 | 1/2007 | Ueno et al. |
| 2007/0015973 A1 | 1/2007 | Nanikashvili et al. |
| 2007/0015976 A1 | 1/2007 | Miesel et al. |
| 2007/0016089 A1 | 1/2007 | Fischell et al. |

(56) References Cited

U.S. PATENT DOCUMENTS

| | | |
|---|---|---|
| 2007/0021678 A1 | 1/2007 | Beck et al. |
| 2007/0021790 A1 | 1/2007 | Kieval et al. |
| 2007/0021792 A1 | 1/2007 | Kieval et al. |
| 2007/0021794 A1 | 1/2007 | Kieval et al. |
| 2007/0021796 A1 | 1/2007 | Kieval et al. |
| 2007/0021797 A1 | 1/2007 | Kieval et al. |
| 2007/0021798 A1 | 1/2007 | Kieval et al. |
| 2007/0021799 A1 | 1/2007 | Kieval et al. |
| 2007/0027388 A1 | 2/2007 | Chou |
| 2007/0027497 A1 | 2/2007 | Parnis |
| 2007/0032749 A1 | 2/2007 | Overall et al. |
| 2007/0038038 A1 | 2/2007 | Stivoric et al. |
| 2007/0038078 A1 | 2/2007 | Osadchy |
| 2007/0038255 A1 | 2/2007 | Kieval et al. |
| 2007/0038262 A1 | 2/2007 | Kieval et al. |
| 2007/0043301 A1 | 2/2007 | Martinsen et al. |
| 2007/0043303 A1 | 2/2007 | Osypka et al. |
| 2007/0048224 A1 | 3/2007 | Howell et al. |
| 2007/0060800 A1 | 3/2007 | Drinan et al. |
| 2007/0060802 A1 | 3/2007 | Ghevondian et al. |
| 2007/0073132 A1 | 3/2007 | Vosch |
| 2007/0073168 A1 | 3/2007 | Zhang et al. |
| 2007/0073181 A1 | 3/2007 | Pu et al. |
| 2007/0073361 A1 | 3/2007 | Goren et al. |
| 2007/0082189 A1 | 4/2007 | Gillette |
| 2007/0083092 A1 | 4/2007 | Rippo et al. |
| 2007/0092862 A1 | 4/2007 | Gerber |
| 2007/0104840 A1 | 5/2007 | Singer |
| 2007/0106132 A1 | 5/2007 | Elhag et al. |
| 2007/0106137 A1 | 5/2007 | Baker, Jr. et al. |
| 2007/0106167 A1 | 5/2007 | Kinast |
| 2007/0118039 A1 | 5/2007 | Bodecker et al. |
| 2007/0123756 A1 | 5/2007 | Kitajima et al. |
| 2007/0123903 A1 | 5/2007 | Raymond et al. |
| 2007/0123904 A1 | 5/2007 | Stad et al. |
| 2007/0129622 A1 | 6/2007 | Bourget et al. |
| 2007/0129643 A1 | 6/2007 | Kwok et al. |
| 2007/0129769 A1 | 6/2007 | Bourget et al. |
| 2007/0142715 A1 | 6/2007 | Banet et al. |
| 2007/0142732 A1 | 6/2007 | Brockway et al. |
| 2007/0149282 A1 | 6/2007 | Lu et al. |
| 2007/0150008 A1 | 6/2007 | Jones et al. |
| 2007/0150009 A1 | 6/2007 | Kveen et al. |
| 2007/0150029 A1 | 6/2007 | Bourget et al. |
| 2007/0162089 A1 | 7/2007 | Mosesov |
| 2007/0167753 A1 | 7/2007 | Van Wyk et al. |
| 2007/0167848 A1 | 7/2007 | Kuo et al. |
| 2007/0167849 A1 | 7/2007 | Zhang et al. |
| 2007/0167850 A1 | 7/2007 | Russell et al. |
| 2007/0172424 A1 | 7/2007 | Roser |
| 2007/0173705 A1 | 7/2007 | Teller et al. |
| 2007/0180047 A1 | 8/2007 | Dong et al. |
| 2007/0180140 A1 | 8/2007 | Welch et al. |
| 2007/0191723 A1 | 8/2007 | Prystowsky et al. |
| 2007/0207858 A1 | 9/2007 | Breving |
| 2007/0208233 A1 | 9/2007 | Kovacs |
| 2007/0208235 A1 | 9/2007 | Besson et al. |
| 2007/0208262 A1 | 9/2007 | Kovacs |
| 2007/0232867 A1 | 10/2007 | Hansmann |
| 2007/0244403 A1 | 10/2007 | Natarajan et al. |
| 2007/0249946 A1 | 10/2007 | Kumar et al. |
| 2007/0250121 A1 | 10/2007 | Miesel et al. |
| 2007/0255120 A1 | 11/2007 | Rosnov |
| 2007/0255153 A1 | 11/2007 | Kumar et al. |
| 2007/0255184 A1 | 11/2007 | Shennib |
| 2007/0255531 A1 | 11/2007 | Drew |
| 2007/0260133 A1 | 11/2007 | Meyer |
| 2007/0260155 A1 | 11/2007 | Rapoport et al. |
| 2007/0260289 A1 | 11/2007 | Giftakis et al. |
| 2007/0273504 A1 | 11/2007 | Tran |
| 2007/0276273 A1 | 11/2007 | Watson, Jr. |
| 2007/0282173 A1 | 12/2007 | Wang et al. |
| 2007/0299325 A1 | 12/2007 | Farrell et al. |
| 2008/0004499 A1 | 1/2008 | Davis |
| 2008/0004904 A1 | 1/2008 | Tran |
| 2008/0021336 A1 | 1/2008 | Dobak |
| 2008/0024293 A1 | 1/2008 | Stylos |
| 2008/0024294 A1 | 1/2008 | Mazar |
| 2008/0033260 A1 | 2/2008 | Sheppard et al. |
| 2008/0039700 A1 | 2/2008 | Drinan et al. |
| 2008/0120784 A1 | 2/2008 | Warner et al. |
| 2008/0058614 A1 | 3/2008 | Banet et al. |
| 2008/0058656 A1 | 3/2008 | Costello et al. |
| 2008/0059239 A1 | 3/2008 | Gerst et al. |
| 2008/0091089 A1 | 4/2008 | Guillory et al. |
| 2008/0114220 A1 | 5/2008 | Banet et al. |
| 2008/0139934 A1 | 6/2008 | McMorrow et al. |
| 2008/0146892 A1 | 6/2008 | LeBoeuf et al. |
| 2008/0167538 A1 | 7/2008 | Teller et al. |
| 2008/0171918 A1 | 7/2008 | Teller et al. |
| 2008/0171922 A1 | 7/2008 | Teller et al. |
| 2008/0171929 A1 | 7/2008 | Katims |
| 2008/0183052 A1 | 7/2008 | Teller et al. |
| 2008/0200774 A1 | 8/2008 | Luo |
| 2008/0214903 A1 | 9/2008 | Orbach |
| 2008/0220865 A1 | 9/2008 | Hsu |
| 2008/0221399 A1 | 9/2008 | Zhou et al. |
| 2008/0221402 A1 | 9/2008 | Despotis |
| 2008/0224852 A1 | 9/2008 | Dicks et al. |
| 2008/0228084 A1 | 9/2008 | Bedard et al. |
| 2008/0275465 A1 | 11/2008 | Paul et al. |
| 2008/0287751 A1 | 11/2008 | Stivoric et al. |
| 2008/0287752 A1 | 11/2008 | Stroetz et al. |
| 2008/0293491 A1 | 11/2008 | Wu et al. |
| 2008/0294019 A1 | 11/2008 | Tran |
| 2008/0294020 A1 | 11/2008 | Sapounas |
| 2008/0318681 A1 | 12/2008 | Rofougaran et al. |
| 2008/0319279 A1 | 12/2008 | Ramsay et al. |
| 2008/0319282 A1 | 12/2008 | Tran |
| 2008/0319290 A1 | 12/2008 | Mao et al. |
| 2009/0005016 A1 | 1/2009 | Eng et al. |
| 2009/0018410 A1 | 1/2009 | Coene et al. |
| 2009/0018456 A1 | 1/2009 | Hung |
| 2009/0048526 A1 | 2/2009 | Aarts et al. |
| 2009/0054737 A1 | 2/2009 | Magar et al. |
| 2009/0062670 A1 | 3/2009 | Sterling et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076401 A1 | 3/2009 | Mazar |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0177145 A1 | 7/2009 | Ohlander |
| 2009/0182204 A1 | 7/2009 | Semler et al. |
| 2009/0234410 A1 | 9/2009 | Libbus et al. |
| 2009/0292194 A1 | 11/2009 | Libbus et al. |
| 2009/0306633 A1 | 12/2009 | Trovato et al. |
| 2010/0056881 A1 | 3/2010 | Libbus et al. |
| 2010/0191310 A1 | 7/2010 | Bly et al. |
| 2011/0144470 A1 | 6/2011 | Mazar et al. |
| 2011/0245711 A1 | 10/2011 | Katra et al. |
| 2011/0257491 A1* | 10/2011 | Robertson ............ A61B 5/0031 600/302 |
| 2011/0270049 A1 | 11/2011 | Katra et al. |

FOREIGN PATENT DOCUMENTS

| | | |
|---|---|---|
| EP | 1579801 A1 | 9/2005 |
| JP | 2005-521448 A | 7/2005 |
| WO | WO 2000/079255 A1 | 12/2000 |
| WO | WO 2001/089362 A2 | 11/2001 |

(56) References Cited

FOREIGN PATENT DOCUMENTS

| WO | WO 02/092101 A1 | 11/2002 |
|----|----|----|
| WO | WO 03/082080 A2 | 10/2003 |
| WO | WO 2005/051164 A2 | 6/2005 |
| WO | WO 2005/104930 A1 | 11/2005 |
| WO | WO 2006/008745 A2 | 1/2006 |
| WO | WO 2006/102476 A2 | 9/2006 |
| WO | WO 2006/111878 A1 | 10/2006 |
| WO | WO 2007/041783 A1 | 4/2007 |
| WO | WO 2007/106455 A2 | 9/2007 |
| WO | WO 2009/116906 A1 | 9/2009 |

OTHER PUBLICATIONS

Acute Decompensated Heart Failure, Wikipedia Entry, downloaded from: http://en.wikipedia.org/wiki/Acute_decompensated_heart_failure, downloaded Feb. 11, 2011, 6 pages.
AD5934: 250kSPS 12-Bit Impedance Converter Network Analyzer, Analog Devices, retrieved from http://www.analog.com/static/imported-files/data_sheets/AD5934.pdf, date unknown, 32 pages.
Adams, Jr., "Guiding heart failure care by invasive hemodynamic measurements: possible or useful?", Journal of Cardiac Failure, vol. 8 (2), 2002, pp. 71-73.
Adamson et al., "Continuous autonomic assessment in patients with symptomatic heart failure: prognostic value of heart rate variability measured by an implanted cardiac resynchronization device", Circulation, vol. 110, 2004, pp. 2389-2394.
Adamson, "Integrating device monitoring into the infrastructure and workflow of routine practice", Rev. Cardiovasc. Med., vol. 7 Suppl 1, 2006, pp. 42-60.
Adamson et al., "Ongoing right ventricular hemodynamics in heart failure", J. Am. Coll. Cardiol, vol. 41, 2003, pp. 565-570.
Adhere, "Insights from the Adhere Registry: Data from over 1000,000 patient cases", Presentation, date unknown, 70 pages.
Advamed, "Health Information Technology: Improving Patient Safety and Quality of Care", Jun. 2005, 23 pages.
Aghababian, "Acutely decompensated heart failure: opportunities to improve care and outcomes in the emergency department", Rev. Cardiovasc. Med., vol. 3 Suppl 4, 2002, pp. S3-9.
Albert, "Bioimpedance to prevent heart failure hospitalization", Curr Heart Fail Rep., vol. 3 (3), Sep. 2006, pp. 136-142.
American Heart Association, "Heart Disease and Stroke Statistics—2006 Update", 2006, 43 pages.
American Heart Association, "Heart Disease and Stroke Statistics—2007 Update", A Report from the American Heart Association Statistics Committee and Stroke Statistics Subcommittee; Circulation, 115, 2007, pp. e69-e171.
Amurthur et al., U.S. Appl. No. 60/972,359, filed Sep. 14, 2007.
Amurthur et al., U.S. Appl. No. 60/972,363, filed Sep. 14, 2007.
Belalcazar et al., "Monitoring lung edema using the pacemaker pulse and skin electrodes", Physiol. Meas., vol. 26, 2005, pp. S153-S163.
Bennett, "Development of implantable devices for continuous ambulatory monitoring of central hemodynamic values in heart failure patients", PACE, vol. 28, Jun. 2005, pp. 573-584.
Bly et al., U.S. Appl. No. 60/972,333, filed Sep. 14, 2007.
Bly et al., U.S. Appl. No. 60/972,629, filed Sep. 14, 2007.
Bly et al., U.S. Appl. No. 61/055,645, filed May 23, 2008.
Bly, U.S. Appl. No. 61/084,567, filed Jul. 29, 2008.
Bourge, "Case studies in advanced monitoring with the chronicle device", Rev Cardiovasc Med., vol. 7 Suppl 1, 2006, pp. S56-S61.
Braunschweig, "Continuous hemodynamic monitoring during withdrawal of diuretics in patients with congestive heart failure", European Heart Journal, vol. 23 (1), 2002, pp. 59-69.
Braunschweig, "Dynamic changes in right ventricular pressures during hemodialysis recorded with an implantable hemodynamic monitor", Nephrol Dial Transplant, vol. 21, 2006, pp. 176-183.
Brennan, "Measuring a Grounded Impedance Profile Using the AD5933", Analog Devices, retrieved from http://www.analog.com/static/imported-files/application_notes/427095282381510189AN847_0.pdf, date unknown, 12 pages.

Buono et al., "The effect of ambient air temperature on whole-body bioelectrical impedance", Physiol. Meas., vol. 25, 2004, pp. 119-123.
Burkhoff et al., "Heart failure with a normal ejection fraction: Is it really a disorder of diastolic function?", Circulation, vol. 107, 2003, pp. 656-658.
Burr et al., "Heart rate variability and 24-hour minimum heart rate", Biological Research for Nursing, vol. 7 (4), 2006, pp. 256-267.
Cardionet, "CardioNet Mobile Cardiac Outpatient Telemetry: Addendum to Patient Education Guide", CardioNet, Inc., 2007, 2 pages.
Cardionet, "Patient Education Guide", CardioNet, Inc., 2007, 7 pages.
Charach et al., "Transthoracic monitoring of the impedance of the right lung in patients with cardiogenic pulmonary edema", Crit Care Med, vol. 29 (6), 2001, pp. 1137-1144.
Charlson et al., "Can disease management target patients most likely to generate high costs? The Impact of Comorbidity", Journal of General Internal Medicine, vol. 22 (4), 2007, pp. 464-469.
Chaudhry et al., "Telemonitoring for patients with chronic heart failure: a systematic review", J Card Fail., vol. 13 (1), Feb. 2007, pp. 56-62.
Chung et al., "White coat hypertension: Not so benign after all?", Journal of Human Hypertension, vol. 17, 2003, pp. 807-809.
Cleland et al., "The EuroHeart Failure survey programme—a survey on the quality of care among patients with heart failure in Europe—Part 1: patient characteristics and diagnosis", European Heart Journal, vol. 24 (5), 2003, pp. 442-463.
Cooley, "The Parameters of Transthoracic Electrical Conduction", Annals of the New York Academy of Sciences, vol. 170 (2), 1970, pp. 702-713.
Cowie et al., "Hospitalization of patients with heart failure. A population-based study", European Heart Journal, vol. 23 (11), 2002, pp. 877-885.
Dimri, "Chapter 1: Fractals in geophysics and semiology: an introduction", Fractal Behaviour of the Earth System, Springer Berlin Heidelberg, Summary and 1st page Only, 2005, pp. 1-22.
El-Dawlatly et al., "Impedance cardiography: noninvasive assessment of hemodynamics and thoracic fluid content during bariatric surgery", Obesity Surgery, vol. 15 (5), May 2005, pp. 655-658.
EM Microelectronic, Marin SA, "Plastic Flexible LCD", Product Brochure, retrieved from http://www.emmicroelectronic.com/Line.asp?IdLine=48, 2009, 2 pages.
Erdmann, "Editorials: The value of diuretics in chronic heart failure demonstrated by an implanted hemodynamic monitor", European Heart Journal, vol. 23 (1), 2002, pp. 7-9.
FDA—Draft questions for Chronicle Advisory Panel Meeting, retrieved from http://www.fda.gov/ohrms/dockets/ac/07/questions/2007-4284q1_draft.pdf, 2007, 3 pages.
FDA—Medtronic Chronicle Implantable Hemodynamic Monitoring System P050032, Panel Package Section 11: Chronicle IBM Summary of Safety and Effectiveness, 2007, 77 pages.
FDA—References for Circulatory System Devices Panel, retrieved from http://www.fda.gov/OHRMS/DOCKETS/AC/07/briefing/2007-4284bibl_01.pdf, Mar. 1, 2007, 1 page.
FDA Executive Summary Memorandum, meeting of the Circulatory Systems Devices Advisory Panel, P050032 Medtronic, Inc. Chronicle Implantable Hemodynamic Monitor (IHM) System, retrieved from http://www.fda.gov.ohrms/dockets/ac/07/briefing/2007-4284b1_02.pdf, Mar. 1, 2007, 23 pages.
FDA Executive Summary, Medtronic Chronicle Implantable Hemodynamic Monitoring System P050032: Executive Summary, Panel Package Sponsor Executive Summary, vol. 1, Sec. 4, retrieved from http://www.fda.gov/OHRMS/DOCKETS/AC/07/briefing/2007-4284b1_03.pdf, 2007, 12 pages.
FDA Panel Recommendation, Chronicle Analysis, Mar. 1, 2007, 14 pages.
FDA—Medtronic Inc., "Chronicle 9520B Implantable Hemodynamic Monitor Reference Manual", 2007, 112 pages.
Flach, U.S. Appl. No. 60/006,600, filed Nov. 13, 1995.
Fonarow, "How well are chronic heart failure patients being managed", Rev Cardiovasc Med., vol. 7 Suppl 1, 2006, pp. S3-11.

(56) References Cited

OTHER PUBLICATIONS

Fonarow, "Maximizing Heart Failure Care", PowerPoint Presentation, downloaded from http://www.medreviews.com/media/MaxHFCore.ppt, date unknown, 130 pages.
Fonarow, "Proactive monitoring and management of the chronic heart failure patient", Rev Cardiovasc Med., vol. 7 Suppl 1, 2006, pp. S1-S2.
Fonarow et al., "Risk stratification for in-hospital mortality in acutely decompensated heart failure: classification and regression tree analysis", JAMA, vol. 293 (5), Feb. 2, 2005, pp. 572-580.
Fonarow, "The Acute Decompensated Heart Failure National Registry (ADHERE): opportunities to improve care of patients hospitalized with acute decompensated heart failure", Rev Cardiovasc Med., vol. 4 Suppl 7, 2003, pp. S21-S30.
Ganion et al., "Intrathoracic impedance to monitor heart failure status: a comparison of two methods in a chronic heart failure dog model", Congest Heart Fail., vol. 11 (4), 2005, pp. 177-181, 211.
Gass et al., "Critical pathways in the management of acute decompensated heart failure: A CME-Accredited monograph", Mount Sinai School of Medicine, 2004, 32 pages.
Gheorghiade et al., "Congestion is an important diagnostic and therapeutic target in heart failure", Rev Cardiovasc Med., vol. 7 Suppl 1, 2006, pp. 12-24.
Gilliam, III et al., "Changes in heart rate variability, quality of life, and activity in cardiac resynchronization therapy patients: results of the HF-HRV registry", Pacing and Clinical Electrophysiology, vol. 30 (1), Jan. 18, 2007, pp. 56-64.
Gilliam, III et al., "Prognostic value of heart rate variability footprint and standard deviation of average 5-minute intrinsic R-R intervals for mortality in cardiac resynchronization therapy patients", J Electrocardiol., vol. 40 (4), Oct. 2007, pp. 336-342.
Gniadecka et al., "Localization of dermal edema in lipodermatosclerosis, lymphedema, and cardiac insufficiency high-frequency ultrasound examination of intradermal echogenicity", J Am Acad oDermatol, vol. 35 (1), Jul. 1996, pp. 37-41.
Goldberg et al., "Randomized trial of a daily electronic home monitoring system in patients with advanced heart failure: The Weight Monitoring in Heart Failure (WHARF) Trial", American Heart Journal, vol. 416 (4), Oct. 2003, pp. 705-712.
Grap et al., "Actigraphy in the Critically Ill: Correlation with Activity, Agitation, and Sedation", American Journal of Critical Care, vol. 14, 2005, pp. 52-60.
Gudivaka et al., "Single and multifrequency models for bioelectrical impedance analysis of body water compartments", J Appl Physiol, vol. 87 (3), 1999, pp. 1087-1096.
Guyton et al., "Unit V: The Body Fluids and Kidneys, Chapter 25: The Body Fluid Compartments: Extracellular and Intracellular Fluids; Interstitial Fluid and Edema", Guyton and Hall Textbook of Medical Physiology 11th Edition, Saunders, 2005, pp. 291-306.
Hadase et al., "Very low frequency power of heart rate variability is a powerful predictor of clinical prognosis in patients with congestive heart failure", Circ J., vol. 68 (4), 2004, pp. 343-347.
Hallstrom et al., "Structural relationships between measures based on heart beat intervals: potential for improved risk assessment", IEEE Biomedical Engineering, vol. 51 (8), 2004, pp. 1414-1420.
Heart Failure, Wikipedia Entry, downloaded from http://en.wikipedia.org/wiki/Heart_failure, downloaded Feb. 11, 2011, 17 pages.
HFSA Comprehensive Heart Failure Practice Guideline—Executive Summary: HFSA Comprehensive Heart Failure Practice Guideline, Journal of Cardiac Failure, vol. 12 (1), 2006, pp. E86-E103.
HFSA Comprehensive Heart Failure Practice Guideline—Section 12: Evaluation and Management of Patients with Acute Decompensated Heart Failure, Journal of Cardiac Failure, vol. 12 (1), 2006, pp. E86-E103.
HFSA Comprehensive Heart Failure Practice Guideline—Section 2: Conceptualization and Working Definition of Heart Failure, Journal of Cardiac Failure, vol. 12 (1), 2006, pp. E10-E11.
HFSA Comprehensive Heart Failure Practice Guideline—Section 4: Evaluation of Patients for Ventricular Dysfunction and Heart Failure, Journal of Cardiac Failure, vol. 12 (1), 2006, pp. E16-E25.
HFSA Comprehensive Heart Failure Practice Guideline—Section 8: Disease Management in Heart Failure Education and Counseling, Journal of Cardiac Failure, vol. 12 (1), 2006, pp. E58-E68.
HFSA Comprehensive Heart Failure Practice Guideline—Section 3: Prevention of Ventricular Remodeling Cardiac Dysfunction, and Heart Failure Overview, Journal of Cardiac Failure, vol. 12 (1), 2006, pp. E12-E15.
HRV Enterprises LLC, "Heart Rate Variability Seminars", downloaded from http://hrventerprise.com, downloaded Apr. 24, 2008, 3 pages.
HRV Enterprises LLC, "LoggerPro HRV Biosignal Analysis", downloaded from http://hrenterprise.com/products.html, downloaded Apr. 24, 2008, 3 pages.
Hunt et al., "ACC/AHA Guideline Update for the Diagnosis and Management of Chronic Heart Failure in the Adult: A Report of the American College of Cardiology/American Heart Association Task Force on Practice Guidelines:", Developed in Collaboration with the American College of Chest Physicians and the International Society for Heart and Lung Transplantation: Endorsed by the Heart Rhythm Society, Circulation, vol. 112, 2005, E154-E235.
Hunt et al., "ACC/AHA Guidelines for the Evaluation and Management of Chronic Heart Failure in the Adult: Executive Summary a Report of the American College of Cardiology/American Heart Association Task Force on Practice Guidelines", Circulation, vol. 104, 2001, pp. 2996-3007.
Imhoff et al., "Noninvasive whole-body electrical bioimpedance cardiac output and invasive thermodilution cardiac output in high-risk surgical patients", Critical Care Medicine, vol. 28 (8), 2000, pp. 21812-2818.
Jaeger et al., "Evidence for Increased Intrathoracic Fluid volume on Man at High Altitude", J Appl Physiol., vol. 47 (6), 1979, pp. 670-676.
Jaio et al., "Variance fractal dimension analysis of seismic refraction signals", WESANEX 97: Communications, Power and Computing, IEEE Conference Proceedings, May 22-23, 1997, pp. 163-167.
Jerant et al., "Reducing the cost of frequent hospital admissions for congestive heart failure: a randomized trial of a home telecare intervention", Medical Care, vol. 39 (11), 2001, pp. 1234-1245.
Kasper et al., "A randomized trial of the efficacy of multidisciplinary care in heart failure outpatients at high risk of hospital readmission", J Am Coll Cardiol, vol. 39, 2002, pp. 471-480.
Kaukinten, "Cardiac output measurement after coronary artery bypass grafting using bolus thermodilution, continuous thermodilution, and whole-body impedance cardiography", Journal of Cardiothoracic and Vascular Anesthesia, vol. 17 (2), 2003, pp. 199-203.
Kawaguchi et al., "Combined ventricular systolic and arterial stiffening in patients with heart failure and preserved ejection fraction: implications for systolic and diastolic reserve limitations", Circulation, vol. 107, 2003, pp. 714-720.
Kawasaki et al., "Heart rate turbulence and clinical prognosis in hypertrophic cardiomyopathy and myocardial infarction", Circ J., vol. 67 (7), 2003, pp. 601-604.
Kearney et al., "Predicting death due to progressive heart failure in patients with mild-to-moderate chronic heart failure", J Am Coll Cardiol, vol. 40 (10), 2002, pp. 1801-1808.
Kitzman et al., "Pathophysiological characterization of isolated diastolic heart failure in comparison to systolic heart failure", Jama, vol. 288 (17), Nov. 2002, pp. 2144-2150.
Koobi et al., "Non-invasive measurement of cardiac output: whole-body impedance cardiography in simultaneous comparison with thermodilution and direct oxygen Fick methods", Intensive Care Medicine, vol. 23 (11), 1997, pp. 1132-1137.
Koyama et al., "Evaluation of heart-rate turbulence as a new prognostic marker in patients with chronic heart failure", Circ J, vol. 66 (10), 2002, pp. 902-907.
Kristofer et al., U.S. Appl. No. 60/972,336, filed Sep. 14, 2007.
Kristofer et al., U.S. Appl. No. 60/972,340, filed Sep. 14, 2007.
Kristofer et al., U.S. Appl. No. 60/972,343, filed Sep. 14, 2007.
Krumholz et al., "Predictors of readmission among elderly survivors of admission with heart failure", American Heart Journal, vol. 139 (1), 2000, pp. 72-77.

(56) References Cited

OTHER PUBLICATIONS

Kyle et al., "Bioelectrical Impedance Analysis—part I: review of principles and methods", Clin Nutr., vol. 23 (5), Oct. 2004, pp. 1226-1243.
Kyle et al., "Bioelectrical Impedance Analysis—part II: utilization in clinical practice", Clin Nutr., vol. 23 (5), Oct. 2004, pp. 1430-1453.
Landrum, U.S. Appl. No. 61/079,746, filed Jul. 10, 2008.
Lee et al., "Predicting mortality among patients hospitalized for heart failure: derivation and validation of a clinical model", JAMA, vol. 290 (19), 2003, pp. 2581-2587.
Leier, "The Physical Examination in Heart Failure—Part I", Congest Hear Fail., vol. 13 (1), Jan.-Feb. 2007, pp. 41-47.
Libbbus et al., U.S. Appl. No. 61/055,662, filed May 23, 2008.
Libbus et al., U.S. Appl. No. 60/972,316, filed Sep. 12, 2008.
Libbus et al., U.S. Appl. No. 60/972,512, filed Sep. 14, 2007.
Libbus et al., U.S. Appl. No. 60/972,581, filed Sep. 14, 2007.
Libbus et al., U.S. Appl. No. 60/972,616, filed Sep. 14, 2007.
Libbus et al., U.S. Appl. No. 61/035,970, filed Mar. 12, 2008.
Libbus et al., U.S. Appl. No. 61/047,875, filed Apr. 25, 2008.
Libbus et al., U.S. Appl. No. 61/055,656, filed May 23, 2008.
LifeShirt Model 200 Directions for Use, Introduction, VivoMetrics, Inc., date unknown, 9 pages.
Liu et al., "Fractal analysis with applications to seismological pattern recognition of underground nuclear explosions", Signal Processing, vol. 80 (9), Sep. 2000, pp. 1849-1861.
Lozano-Nieto, "Impedance ratio in bioelectrical impedance measurements for body fluid shift determination", Proceedings of the IEEE 24th Annual Northeast Bioengineering Conference, Apr. 9-10, 1998, pp. 24-25.
Lucreziotti et al., "Five-minute recording of heart rate variability in severe chronic heart failure: Correlates with right ventricular function and prognostic implications", American Heart Journal, vol. 139 (6), 2000, pp. 1088-1095.
Luthje et al., "Detection of heart failure decompensation using intrathoracic impedance monitoring by a triple-chamber implantable defibrillator", Heart Rhythm, vol. 2 (9), Sep. 2005, pp. 997-999.
Magalski et al., "Continuous ambulatory right heart pressure measurements with an implantable hemodynamic monitor: a multicenter, 12-Month Follow-Up Study of Patients with Chronic Heart Failure", J Card Fail, vol. 8 (2), 2002, pp. 63-70.
Mahlberg et al., "Actigraphy in agitated patients with dementia: Monitoring treatment outcomes", Zeitschrift fur Gerontologie and Geriatric, vol. 40 (3), Jun. 2007, pp. 178-184.
Manicka et al., U.S. Appl. No. 60/972,329, filed Sep. 14, 2007.
Manicka et al., U.S. Appl. No. 60/972,537, filed Sep. 14, 2007.
Manicka et al., U.S. Appl. No. 61/055,666, filed May 23, 2008.
Matthie et al., "Analytic assessment of the various bioimpedance methods used to estimate body water", Appl Physiol, vol. 84 (5), 1998, pp. 1801-1816.
Matthie et al., "Second generation mixture theory equation for estimating intracellular water using bioimpedance spectroscopy", J Appl Physiol, vol. 99, 2005, pp. 780-781.
Mazar et al., U.S. Appl. No. 60/972,354, filed Sep. 14, 2007.
Mazar, U.S. Appl. No. 61/046,196, filed Apr. 18, 2008.
McMurray et al., "Heart Failure: Epidemiology, Aetiology, and Prognosis of Heart Failure", Heart, vol. 83, 2000, pp. 596-602.
Miller, "Home monitoring for congestive heart failure patients", Caring Magazine, Aug. 1995, pp. 53-54.
Moser et al., "Improving outcomes in heart failure: it's not unusual beyond usual Care", Circulation, vol. 105, 2002, pp. 2810-2812.
Nagels et al., "Actigraphic measurement of agitated behaviour in dementia", International Journal of Geriatric Psychiatry, vol. 21 (4), 2009, pp. 388-393.
Nakamura et al., "Universal scaling law in human behavioral organization", Physical Review Letters, vol. 99 (13), Sep. 28, 2007, 4 pages.
Nakaya, "Fractal properties of seismicity in regions affected by large, shallow earthquakes in western Japan: Implications for fault formation processes based on a binary fractal fracture network model", Journal of Geophysical Research, vol. 11 (B1), Jan. 2005, pp. B01310.1-B01310.15.
Naylor et al., "Comprehensive discharge planning for the hospitalized elderly: a randomized clinical trial", Amer. College Physicians, vol. 120 (12), 1994, pp. 999-1006.
Nesiritide (NATRECOR), "Acutely Decompensated Congestive Heart Failure: Burden of Disease", Presentation, downloaded from http://www.huntsvillehospital.org/foundation/events/cardiologyupdate/CHF.ppt, date unknown, 39 pages.
Nieminen et al., "EuroHeart Failure Survey II (EHFSII): a survey on hospitalized acute heart failure patients: description of population", European Heart Journal, vol. 27 (22), 2006, pp. 2725-2736.
Nijsen et al., "The potential value of three-dimensional accelerometry for detection of motor seizures in severe epilepsy", Epilepsy Behav., vol. 7 (1), Aug. 2005, pp. 74-84.
Noble et al., "Diuretic induced change in lung water assessed by electrical impedance tomography", Physiol. Meas., vol. 21 (1), 2000, pp. 155-163.
Noble et al., "Monitoring patients with left ventricular failure by electrical impedance tomography", Eur J Heart Fail., vol. 1 (4), Dec. 1999, pp. 379-384.
O'Connell et al., "Economic impact of heart failure in the United States: time for a different approach", J Heart Lung Transplant., vol. 13 (4), Jul.-Aug. 1994, p. S107-S112.
Ohlsson et al., "Central hemodynamic responses during serial exercise tests in heart failure patients using implantable hemodynamic monitors", Eur J Heart Fail., vol. 5 (3), Jun. 2003, pp. 253-259.
Ohlsson et al., "Continuous ambulatory monitoring of absolute right ventricular pressure and mixed venous oxygen saturation in patients with heart failure using an implantable hemodynamic monitor", European Heart Journal, vol. 22 (11), 2001, pp. 942-954.
Packer et al., "Utility of impedance cardiography for the identification of short-term risk of clinical decompensation in stable patients with chronic heart failure", J. Am. Coll Cardiol, vol. 47 (11), 2006, pp. 2245-2252.
Palatini et al., "Predictive value of clinic and ambulatory heart rate for mortality in elderly subjects with systolic hypertension", Arch Intern Med., vol. 162, 2002, pp. 2313-2321.
Piiria et al., "Crackles in patients with fibrosing alveolitis bronchiectasis, COPD, and Heart Failure", Chest, vol. 99 (5), May 1991, pp. 1076-1083.
Pocock et al., "Predictors of mortality in patients with chronic heart failure", Eur Heart J, vol. 27, 2006, pp. 65-75.
Poole-Wilson et al., "Importance of control of fluid volumes in heart failure", European Heart Journal, vol. 22 (11), 2000, pp. 893-894.
Raj et al., "Letter Regarding Article by Adamson et al. Continuous Autonomic Assessment in Patients with Symptomatic Heart Failure: Prognostic Value of Heart Rate Variability Measured by an Implanted Cardiac Resynchronization Device", Circulation, vol. 112, 2005, pp. E37-E38.
Ramirez et al., "Prognostic value of hemodynamic findings from impedance cardiography in hypertensive stroke", AJH, vol. 18 (20), 2005, pp. 65-72.
Rich et al., "A multidisciplinary intervention to prevent the readmission of elderly patients with congestive heart failure", New Engl. J. Med., vol. 333, 1995, pp. 1190-1195.
Roglieri et al., "Disease management interventions to improve outcomes in congestive heart failure", Am J. Manag Care., vol. 3 (12), Dec. 1997, pp. 1831-1839.
Sahalos et al., "The electrical impedance of the human thorax as a guide in evaluation of intrathoracic fluid volume", Phys. Med. Biol., vol. 31, 1986, pp. 425-439.
Saxon et al., "Remote active monitoring in patients with heart failure (rapid-rf): design and rationale", Journal of Cardiac Failure, vol. 13 (4), 2007, pp. 241-246.
Scharf et al., "Direct digital capture of pulse oximetry waveforms", Proceedings of the Twelfth Southern Biomedical Engineering Conference, 1993, pp. 230-232.
Shabetai, "Monitoring heart failure hemodynamics with an implanted device: its potential to improve outcome", J Am Coll Cardiol, vol. 41, 2003, pp. 572-573.

(56) References Cited

OTHER PUBLICATIONS

Small, "Integrating monitoring into the infrastructure and workflow of routine practice: OptiVol", Rev Cardiovasc Med., vol. 7 Supp 1, 2006, pp. S47-S55.
Smith et al., "Outcomes in heart failure patients with preserved ejection fraction: mortality, readmission, and functional decline", J Am Coll Cardiol, vol. 41, 2003, pp. 1510-1518.
Starling, "Improving care of chronic heart failure: advances from drugs to devices", Cleveland Clinic Journal of Medicine, vol. 70 (2), Feb. 2003, pp. 141-146.
Steijaert et al., "The use of multi-frequency impedance to determine total body water and extracellular water in obese and lean female individuals", International Journal of Obesity, vol. 21 (10), Oct. 1997, pp. 930-934.
Stewart et al., "Effects of a home-based intervention among patients with congestive heart failure discharged from acute hospital care", Arch Intern Med., vol. 158, 1998, pp. 1067-1072.
Stewart et al., "Effects of a multidisciplinary, home-based intervention on planned readmissions and survival among patients with chronic congestive heart failure: a randomized controlled study", The Lancet, vol. 354 (9184), Sep. 1999, pp. 1077-1083.
Stewart et al., "Home-based intervention in congestive heart failure: long-term implications on readmission and survival", Circulation, vol. 105, 2002, pp. 2861-2866.
Stewart et al., "Prolonged beneficial effects of a home-based intervention on unplanned readmissions and mortality among patients with congestive heart failure", Arch Intern Med., vol. 159, 1999, pp. 257-261.
Stewart et al., "Trends in Hospitalization for Heart Failure in Scotland. An Epidemic that has Reached Its Peak?", European Heart Journal, vol. 22 (3), 2001, pp. 209-217.
Swedberg et al., "Guidelines for the diagnosis and treatment of chronic heart failure: executive summary: The task force for the diagnosis and treatment of chronic heart failure of the European Society of Cardiology", Eur Heart J., vol. 26 (11), Jun. 2005, pp. 1115-1140.
Tang, "Case studies in advanced monitoring: OptiVol", Rev Cardiovasc Med., vol. 7 Suppl 1, 2006, pp. S62-S66.
The Economist, "Something in the way he moves", retrieved from http://www.economist.com/science/printerFriendly.cfm?storyid=9861412, 2007.
The Escape Investigators, and Escapie Study Coordinators, "Evaluation Study of Congestive Heart Failure and Pulmonary Artery Catheterization Effectiveness", JAMA, vol. 294, 2005, pp. 1625-1633.
Tosi et al., "Seismic signal detection by fractal dimension analysis", Bulletin of the Seismological Society of America, vol. 89 (4), Aug. 1999, pp. 970-977.
Van De Water et al., "Monitoring the chest with impedance", Chest, vol. 64, 1973, pp. 597-603.
Van Someren, "Actigraphic monitoring of movement and rest-activity rhythms in aging, Alzheimer's disease, and Parkinson's disease", IEEE Transactions on Rehabilitation Engineering, vol. 5 (4), Dec. 1997, pp. 394-398.
Vasan et al., "Congestive heart failure in subjects with normal versus reduced left ventricular ejection fraction", J Am Coll Cardiol, vol. 33, 1999, pp. 1948-1955.
Verdecchia et al., "Adverse prognostic value of an blunted circadian rhythm of heart rate in essential hypertension", Journal of Hypertension, vol. 16 (9), 1998, pp. 1335-1343.
Verdecchia et al., "Ambulatory pulse pressure: a potent predictor of total cardiovascular risk in hypertension", Hypertension, vol. 32, 1998, pp. 983-988.
Vollmann et al., "Clinical utility of intrathoracic impedance monitoring to alert patients with an implanted device of deteriorating chronic heart failure", European Heart Journal Advance Access, downloaded from http://eurheartj.oxfordjournals.org/cgi/content/full/ehl506v1, Feb. 19, 2007, 6 pages.
Vuksanovic et al., "Effect of posture on heart rate variability spectral measures in children and young adults with heart disease", International Journal of Cardiology, vol. 101 (2), 2005, pp. 273-278.
Wang et al., "Feasibility of using an implantable system to measure thoracic congestion in an ambulatory chronic heart failure canine model", PACE, vol. 28 (5), 2005, pp. 404-411.
Wickemeyer et al., "Association between atrial and ventricular tachyarrhythmias, intrathoracic impedance and heart failure decompensation in CRT-D Patients", Journal of Cardiac Failure, vol. 13 (6), 2007, pp. S131-S132.
Williams et al., "How do different indicators of cardiac pump function impact upon the long-term prognosis of patients with chronic heart failure", American Heart Journal, vol. 150 (5), date unknown, pp. E1-E983.
Wonisch et al., "Continuous hemodynamic monitoring during exercise in patients with pulmonary hypertension", Int J Cardiol., vol. 101 (3), Jun. 8, 2005, pp. 415-420.
Wynne et al., "Impedance cardiography: a potential monitor for hemodialysis", Journal of Surgical Research, vol. 133 (1), 2006, pp. 55-60.
Yancy, "Current approaches to monitoring and management of heart failure", Rev Cardiovasc Med., vol. 7 Suppl 1, 2006, pp. S25-S32.
Ypenburg et al., "Intrathoracic Impedance Monitoring of Predict Decompensated Heart Failure", Am J Cardiol, vol. 99 (4), 2007, pp. 554-557.
Yu et al., "Intrathoracic Impedance Monitoring in Patients with Heart Failure: Correlation with Fluid Status and Feasibility of Early Warning Preceding Hospitalization", Circulation, vol. 112, 2005, pp. 841-848.
Zannad et al., "Incidence, clinical and etiologic features, and outcomes of advanced chronic heart failure: The Epical Study", J Am Coll Cardiol, vol. 33 (3), 1999, pp. 734-742.
Zile, "Heart failure with preserved ejection fraction: is this diastolic heart failure?", J Am Coll Cardiol., vol. 41 (9), 2003, pp. 1519-1522.
3M Corporation, "3M Surgical Tapes—Choose the Correct Tape", quicksheet, 2004.

\* cited by examiner

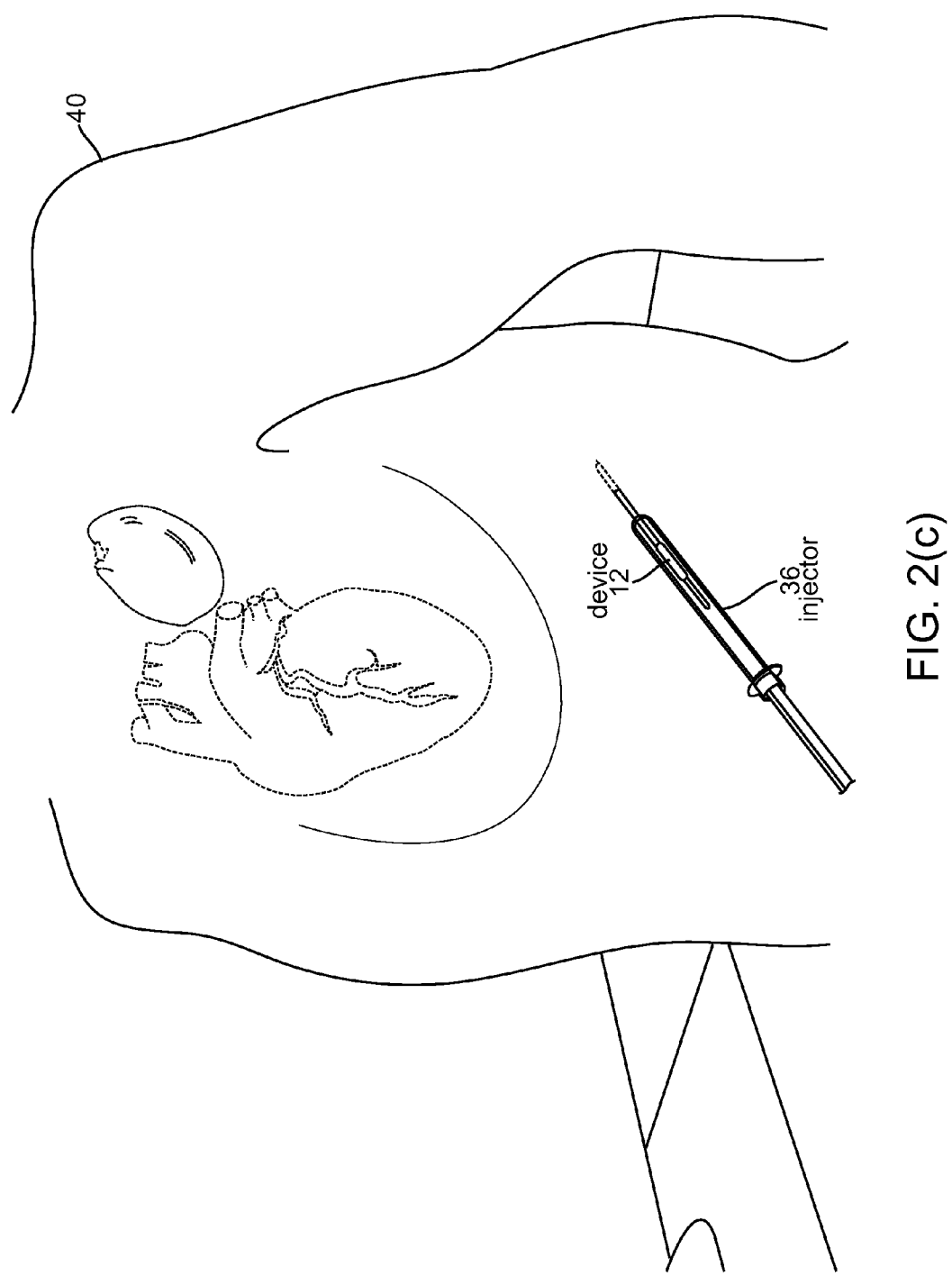

INJECTABLE DEVICE FOR PHYSIOLOGICAL MONITORING

CROSS-REFERENCES TO RELATED APPLICATIONS

The present application is a continuation of pending U.S. patent application Ser. No. 12/209,430 filed Sep. 12, 2008 and titled "Injectable Device for Physiological Monitoring", which claims the benefit under 35 USC 119(e) of U.S. Provisional Application Nos. 60/972,329, 60/972,336, 60/972,354 and 60/972,537, all filed Sep. 14, 2007, and 61/055,666 filed May 23, 2008; the full disclosures of which are incorporated herein by reference in their entirety.

The subject matter of the present application is related to the following applications: 60/972,512; 60/972,616; 60/972,363; 60/972,343; 60/972,581; 60/972,629; 60/972,316; 60/972,333; 60/972,359; 60/972,336; 60/972,340 all of which were filed on Sep. 14, 2007; 61/046,196 filed Apr. 18, 2008; 61/047,875 filed Apr. 25, 2008; 61/055,645, 61/055,656, 61/055,662, all filed May 23, 2008; and 61/079,746 filed Jul. 10, 2008.

The following applications are being filed concurrently with the present application, on Sep. 12, 2008: U.S. patent application Ser. No. 12/209,279 entitled "Multi-Sensor Patient Monitor to Detect Impending Cardiac Decompensation Prediction"; U.S. patent application Ser. No. 12/209,288 entitled "Adherent Device with Multiple Physiological Sensors"; U.S. patent application Ser. No. 12/209,479 entitled "Injectable Physiological Monitoring System"; U.S. patent application Ser. No. 12/209,262 entitled "Adherent Device for Cardiac Rhythm Management"; U.S. patent application Ser. No. 12/209,268 entitled "Adherent Device for Respiratory Monitoring"; U.S. patent application Ser. No. 12/209,269 entitled "Adherent Athletic Monitor"; U.S. patent application Ser. No. 12/209,259 entitled "Adherent Emergency Monitor"; U.S. patent application Ser. No. 12/209,273 entitled "Adherent Device with Physiological Sensors"; U.S. patent application Ser. No. 12/209,276 entitled "Medical Device Automatic Start-up upon Contact to Patient Tissue"; U.S. patent application Ser. No. 12/210,078 entitled "System and Methods for Wireless Body Fluid Monitoring"; U.S. patent application Ser. No. 12/209,265 entitled "Adherent Cardiac Monitor with Advanced Sensing Capabilities"; U.S. patent application Ser. No. 12/209,292 entitled "Adherent Device for Sleep Disordered Breathing"; U.S. patent application Ser. No. 12/209,278 entitled "Dynamic Pairing of Patients to Data Collection Gateways"; U.S. patent application Ser. No. 12/209,508 entitled "Adherent Multi-Sensor Device with Implantable Device Communications Capabilities"; U.S. patent application Ser. No. 12/209,528 entitled "Data Collection in a Multi-Sensor Patient Monitor"; U.S. patent application Ser. No. 12/209,271 entitled "Adherent Multi-Sensor Device with Empathic Monitoring"; U.S. patent application Ser. No. 12/209,274 entitled "Energy Management for Adherent Patient Monitor"; and U.S. patent application Ser. No. 12/209,294 entitled "Tracking and Security for Adherent Patient Monitor."

BACKGROUND OF THE INVENTION

Field of the Invention

This invention relates generally to systems and methods for remote patient monitoring, and more particularly, to systems and methods for remote patient monitoring with percutaneously implanted sensors.

Frequent monitoring of patients permits the patients' physician to detect worsening symptoms as they begin to occur, rather than waiting until a critical condition has been reached. As such, home monitoring of patients with chronic conditions is becoming increasingly popular in the health care industry for the array of benefits it has the potential to provide. Potential benefits of home monitoring are numerous and include: better tracking and management of chronic disease conditions, earlier detection of changes in the patient condition, and reduction of overall health care expenses associated with long term disease management. The home monitoring of a number of diverse "chronic diseases" is of interest, where such diseases include diabetes, dietary disorders such as anorexia and obesity, depression, anxiety, epilepsy, respiratory diseases, AIDS and other chronic viral conditions, conditions associated with the long term use of immunosuppressant's, e.g., in transplant patients, asthma, chronic hypertension, chronic use of anticoagulants, and the like.

Of particular interest in the home monitoring sector of the health care industry is the remote monitoring of patients with heart failure (HF), also known as congestive heart failure. HF is a syndrome in which the heart is unable to efficiently pump blood to the vital organs. Most instances of HF occur because of a decreased myocardial capacity to contract (systolic dysfunction). However, HF can also result when an increased pressure-stroke-volume load is imposed on the heart, such as when the heart is unable to expand sufficiently during diastole to accommodate the ventricular volume, causing an increased pressure load (diastolic dysfunction).

In either case, HF is characterized by diminished cardiac output and/or damming back of blood in the venous system. In HF, there is a shift in the cardiac function curve and an increase in blood volume caused in part by fluid retention by the kidneys. Indeed, many of the significant morphologic changes encountered in HF are distant from the heart and are produced by the hypoxic and congestive effects of the failing circulation upon other organs and tissues. One of the major symptoms of HF is edema, which has been defined as the excessive accumulation of interstitial fluid, either localized or generalized.

HF is the most common indication for hospitalization among adults over 65 years of age, and the rate of admission for this condition has increased progressively over the past two decades. It has been estimated that HF affects more than 3 million patients in the U.S. (O'Connell, J. B. et al., *J. Heart Lung Transpl.*, 13(4):S107-112 (1993)).

In the conventional management of HF patents, where help is sought only in crisis, a cycle occurs where patients fail to recognize early symptoms and do not seek timely help from their care-givers, leading to emergency department admissions (Miller, P. Z., *Home monitoring for congestive heart failure patients*, Caring Magazine, 53-54 (August 1995)). Recently, a prospective, randomized trial of 282 patients was conducted to assess the effect of the intervention on the rate of admission, quality of life, and cost of medical care. In this study, a nurse-directed, multi-disciplinary intervention (which consisted of comprehensive education of the patient and family, diet, social-service consultation and planning, review of medications, and intensive assessment of patient condition and follow-up) resulted in fewer readmissions than the conventional treatment group and a concomitant overall decrease in the cost of care (Rich, M. W. et al., *New Engl. J. Med.*, 333:1190-95 (1995)).

Similarly, comprehensive discharge planning and a home follow-up program was shown to decrease the number of readmissions and total hospital charges in an elderly population (Naylor, M. et al., *Amer. College Physicians*, 120: 999-1006 (1994)). Therefore, home monitoring is of particular interest in the HF management segment of the health care industry.

Another area in which home-monitoring is of particular interest is in the remote monitoring of a patient parameter that provides information on the titration of a drug, particularly with drugs that have a consequential effect following administration, such as insulin, anticoagulants, ACE inhibitors, beta-blockers, diuretics and the like.

Although a number of different home monitoring systems have been developed, there is continued interest in the development of new monitoring systems. Of particular interest would be the development of a system that provides for improved patient compliance, ease of use, etc. Of more particular interest would be the development of such a system that is particularly suited for use in the remote monitoring of patients suffering from HF.

Subcutaneous implantation of sensors has been achieved with an insertion and tunneling tool. The tunneling tool includes a stylet and a peel-away sheath. The tunneling tool is inserted into an incision and the stylet is withdrawn once the tunneling tool reaches a desired position. An electrode segment is inserted into the subcutaneous tunnel and the peel-away sheath is removed. In another delivery device, a pointed tip is inserted through the skin and a plunger is actuated to drive the sensor to its desired location.

In other delivery systems, an implant trocar includes a cannula for puncturing the skin and an obturator for delivering the implant. A spring element received within the cannula prevents the sensor from falling out during the implant process. Another sensor delivery device includes an injector that has a tubular body divided into two adjacent segments with a hollow interior bore. A pair of laterally adjacent tines extend longitudinally from the first segment to the distal end of the tubular body. A plunger rod has an exterior diameter just slightly larger than the interior diameter of the tubular body. With the second segment inserted beneath the skin, the push rod is advanced longitudinally through the tubular body, thereby pushing the sensor through the bore. As the implant and rod pass through the second segment, the tines are forced radially away from each other, thereby dilating or expanding the incision, and facilitating implant. The instrument is removed from the incision following implantation.

For the above and other reasons, it would be desirable to provide an improved percutaneous sensor device for physiological monitoring.

BRIEF SUMMARY OF THE INVENTION

In a first aspect, embodiments of the present invention provide an injectable detecting device for use in physiological monitoring is provided. The device comprises a plurality of sensors axially spaced along a body that provide an indication of at least one physiological event of a patient, a monitoring unit within the body coupled to the plurality of sensors configured to receive data from the plurality of sensors and create processed patient data, a power source within the body coupled to the monitoring unit, and a communication antenna external to the body coupled to the monitoring unit configured to transfer data to/from other devices.

In many embodiments, the monitoring unit includes a processor. In many embodiments, the processor includes program instructions for evaluating values received from the sensors with respect to acceptable physiological ranges for each value received by the processor and determine variances.

In many embodiments, the monitoring unit includes logic resources that determine heart failure status and predict impending decompensation.

In many embodiments, the monitoring unit is configured to perform one or more of, data compression, prioritizing of sensing by a sensor, cycling sensors, monitoring all or some of sensor data by all or a portion of the sensors, sensing by the sensors in real time, noise blanking to provide that sensor data is not stored if a selected noise level is determined, low-power of battery caching and decimation of old sensor data.

In many embodiments, the monitoring unit includes a notification device configured to provide notification when values received from the plurality of sensors are not within acceptable physiological ranges.

In many embodiments, the monitoring unit is configured to serve as a communication hub for multiple medical devices, coordinating sensor data and therapy delivery while transmitting and receiving data from a remote monitoring system.

In many embodiments, the monitoring unit is configured to deactivate selected sensors to reduce redundancy.

In many embodiments, each of a sensor is selected from at least one of, bioimpedance, heart rate, heart rhythm, HRV, HRT, heart sounds, respiratory sounds, respiratory rate and respiratory rate variability, blood pressure, activity, posture, wake/sleep, orthopnea, temperature, heat flux and an accelerometer.

In many embodiments, each of a sensor is an activity sensor selected from at least one of, ball switch, accelerometer, minute ventilation, HR, bioimpedance noise, skin temperature/heat flux, BP, muscle noise and posture.

In many embodiments, the sensors are made of at least a material selected from, silicone, polyurethane, Nitinol, titanium, a biocompatible material, ceramics and a bioabsorbable material.

In many embodiments, at least a portion of sensors of the plurality of sensors have an insulative material selected from, PEEK, ETFE, PTFE, and polyimide, silicon, polyurethane.

In many embodiments, at least a portion of sensors of the plurality of sensors have openings or an absorbent material configured to sample a hydration level or electrolyte level in a surrounding tissue site of the plurality of sensors.

In many embodiments, the plurality of sensors includes current delivery electrodes and sensing electrodes.

In many embodiments, the outputs of the plurality of sensors is used to calculate and monitor blended indices. The blended indices include at least one of, heart rate (HR) or respiratory rate (RR) response to activity, HR/RR response to posture change, HR+RR, HR/RR+bioimpedance, and/or minute ventilation/accelerometer.

In many embodiments, the body and antenna are injectable in the patient by at least one of, catheter delivery, blunt tunneling, insertion with a needle, by injection, with a gun or syringe device with a stiffening wire stylet, guidewire, or combination of stylet or guidewire with a catheter.

In many embodiments, the body is flexible.

In many embodiments, at least a portion of the body has a drug eluting coating.

In many embodiments, the power source comprises a rechargeable battery transcutaneously chargeable with an external unit.

BRIEF DESCRIPTION OF THE DRAWINGS

FIG. 2(c) illustrates the device of FIG. 2(a) in the injector and ready to be introduced into the patient.

DETAILED DESCRIPTION OF THE INVENTION

Figure 1:
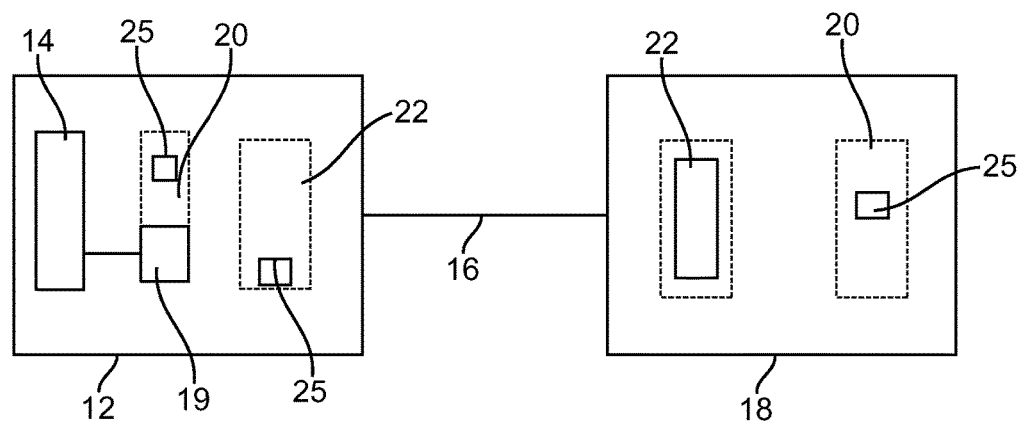
FIG. 1 is a block diagram illustrating one embodiment of a patient monitoring system of the present invention.

The present invention is directed to a heart failure patient management system consisting of one or more subcutaneously injectable devices inserted below the patient's skin. The system continuously monitors physiological parameters, communicates wirelessly with a remote center, and provides alerts when necessary.

The heart failure patient management system monitors physiological parameters and uses a proprietary algorithm to determine heart failure status and predict impending decompensation. The one or more injectable devices communicate with a remote center, preferably via an intermediate device in the patient's home. In some embodiments, the injectable device monitoring unit receives the data and applies the prediction algorithm. When a flag is raised, the center may communicate with the patient, hospital, nurse, and/or physician to allow for therapeutic intervention to prevent decompensation.

The injectable devices would perform the following functions: initiation, programming, measuring, storing, analyzing, communicating, predicting, and displaying.

The system contains one or more injectable devices, each consisting of a hermetically sealed package containing and contains a power source, memory, logic, wireless communication capabilities, and a subset of the following physiological sensors: bioimpedance, heart rate (ave, min, max), heart rhythm, HRV, HRT, heart sounds (e.g. S3), respiratory sounds, blood pressure, activity, posture, wake/sleep, orthopnea, and temperature/heat flux. The activity sensor may be one of the following: ball switch, accelerometer, minute ventilation, HR, bioimpedance noise, skin temperature/heat flux, BP, muscle noise, and posture.

The injectable devices may communicate directly with each other, allow for coordinated sensing between the units. The injectable devices may also communicate with an external unit (either adherent, wearable, or non-wearable) or with an implantable device, such as a cardiac rhythm management device.

The injectable devices wirelessly communicates with a remote center. Such communication may occur directly (via a cellular or Wi-Fi network), or indirectly through an intermediate device. The intermediate device may consist of multiple devices which communicate wired or wirelessly to relay data to the remote center.

The injectable devices may have a rechargeable battery, which is transcutaneously charged with an external unit.

The injectable device package may contain one or more features to allow for tissue anchoring. Such features may include passive or actively-deployed barbs or anchors, tissue adhesion pads, and/or suture loops. Tissue adhesion pads (or grooves or holes) may be designed to be small enough to stabilize the device while allowing for easy extraction.

The injectable devices may use one or more of the following component technologies: flex circuits, thin film resistors, and organic transistors.

The injectable devices may have one of the following form factors: cylinder, dog-bone, half dog-bone, trapezoidal cross-section, semicircular cross-section, star-shaped cross-section, v-shaped cross-section, helical/spiral, fin electrodes, and linear device with a radius of curvature to match radius of implant site.

The injectable devices may be constructed of one or more of the following materials: silicone, polyurethane, Nitinol, a biocompatible material, and a bioabsorbable material. The electrodes may use one or more of the following metal conductors: platinum, MP35N, MP35N/Ag core, platinum/tantalum core, stainless steel, and titanium. Insulative materials may include one or more of the following: PEEK, ETFE, PTFE, and polyimide. Ceramics may be used to enclose electronics (especially the RF unit, to enable RF transmission).

The injectable devices may contain a drug eluting coating, which would slowly release a drug such as an antibiotic or anti-inflammatory agent.

The injectable devices may contain openings and/or absorbent material, through which the device may sample the hydration level and/or electrolytes in the surrounding tissue.

The injectable devices may include multiple features to enhance physiological sensing performance. Such features may include multiple sensing vectors, including redundant vectors. This configuration would allow the injectable devices to determine the optimal sensing configuration, and electronically reposition each sensing vector.

The injectable device electrodes may be partially masked to minimize contamination of the sensed signal. The size and shape of current delivery electrodes (for bioimpedance) and sensing electrodes would be optimized to maximize sensing performance.

While the present invention is intended for heart failure patient monitoring, the system may be applicable to any human application in which wireless physiological monitoring and prediction is required.

The percutaneous sensing device may be used in conjunction with remote patient monitoring to track a patient's physiological status, detect and predict negative physiological events. In one embodiment, the implanted sensing device includes a plurality of sensors that are used in combination to enhance detection and prediction capabilities as more fully explained below.

In one embodiment, illustrated in FIG. 1, the system 10 includes an injectable detecting system 12 that includes a plurality of sensors 14 and/or electrodes, that provide an indication of at least one physiological event of a patient. The injectable detecting system 12 is inserted subcutaneously. In one embodiment the injectable detecting system 12 is inserted in the patient's thorax. The system 10 also includes a wireless communication device 16, coupled to the plurality of sensors 14. The wireless communication device transfers patient data directly or indirectly from the plurality of sensors 14 to a remote monitoring system 18. The remote monitoring system 18 uses data from the sensors to determine the patient's status. The system 10 can continuously, or non-continuously, monitor the patient, alerts are provided as necessary and medical intervention is provided when required. In one embodiment, the wireless communication device 16 is a wireless local area network for receiving data from the plurality of sensors.

The sensors 14 are subcutaneously inserted with the injectable detecting system 12 that is catheter based, blunt tunneling (with either a separate tunneling tool or a wire-stiffened lead), needle insertion gun or syringe-like injection. The injectable detecting system 12 can be flexible, and be used with a stiffening wire, stylet, catheter or guidewire. The injectable detecting system 12 can include any of the following to assist in subsequent extraction: (i) an isodiametric profile, (ii) a breakaway anchor, (iii) a bioabsorbable material, (iv) coatings to limit tissue in-growth, (v) an electrically activated or fusable anchor, and the like. The injectable detecting system 12 can be modular, containing multiple connected components, a subset of which is easily extractable.

The injectable detecting system 12 can be inserted in the patient in a non-sterile or sterile setting, non-surgical setting or surgical setting, implanted with our without anesthesia and implanted with or without imaging assistance from an imaging system. The injectable detecting system 12 can be anchored in the patient by a variety of means including but not limited to, barbs, anchors, tissue adhesion pads, suture loops, with sensor shapes that conform to adjacent tissue anatomy or provide pressure against the adjacent tissue, with the use of self-expanding materials such as a nitinol anchor and the like.

Figure 2A:
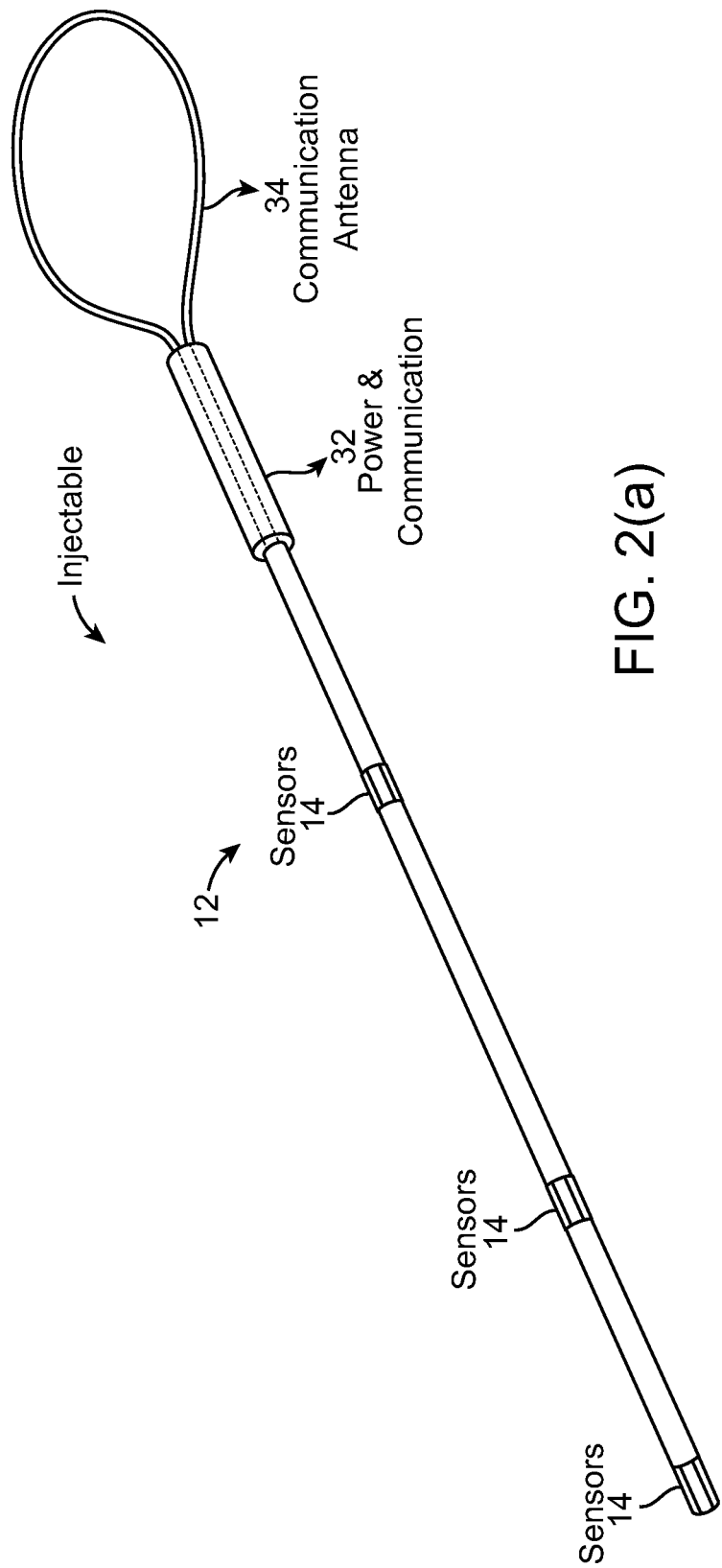
FIG. 2(a) illustrates one embodiment of an implanted sensor device of the present invention that is injectable and includes multiple sensors, power and communication and a communication antenna.
Figure 2B:
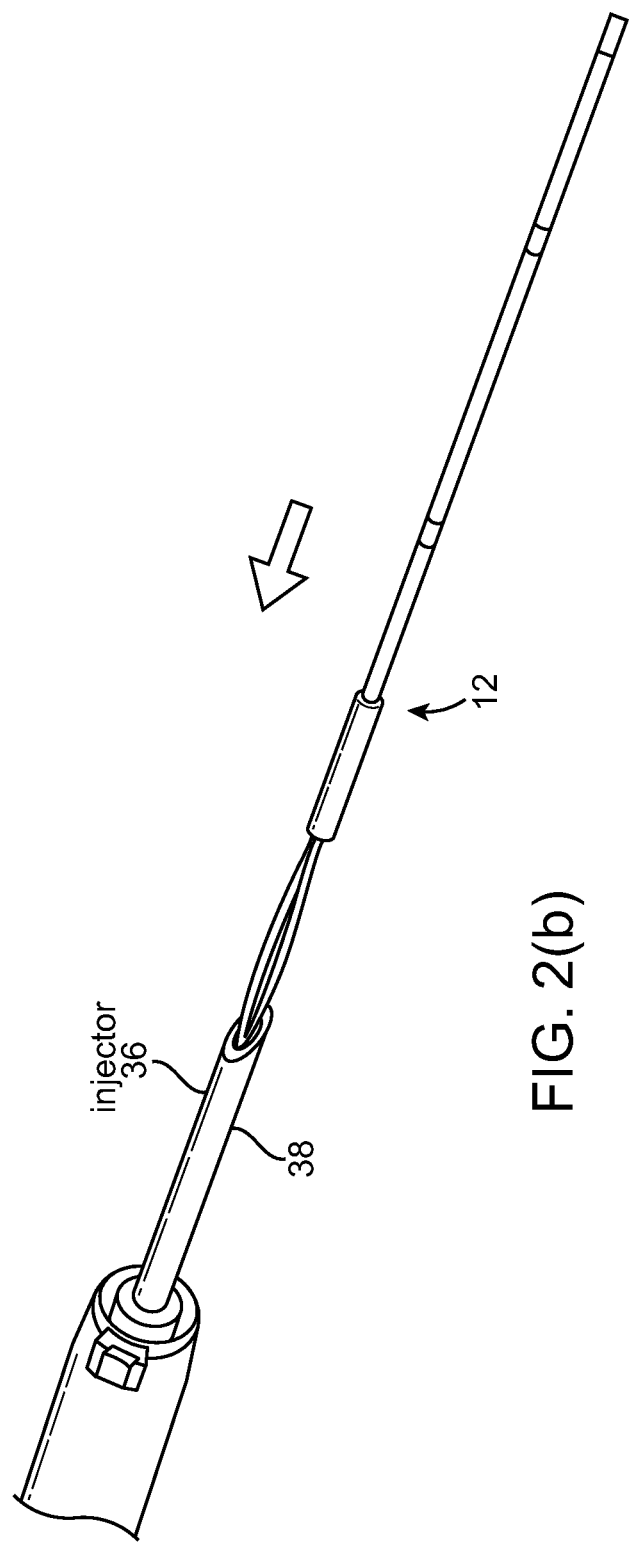
FIG. 2(b) illustrates the insertion of the device of FIG. 2(a) into an injector.
Figure 2D:
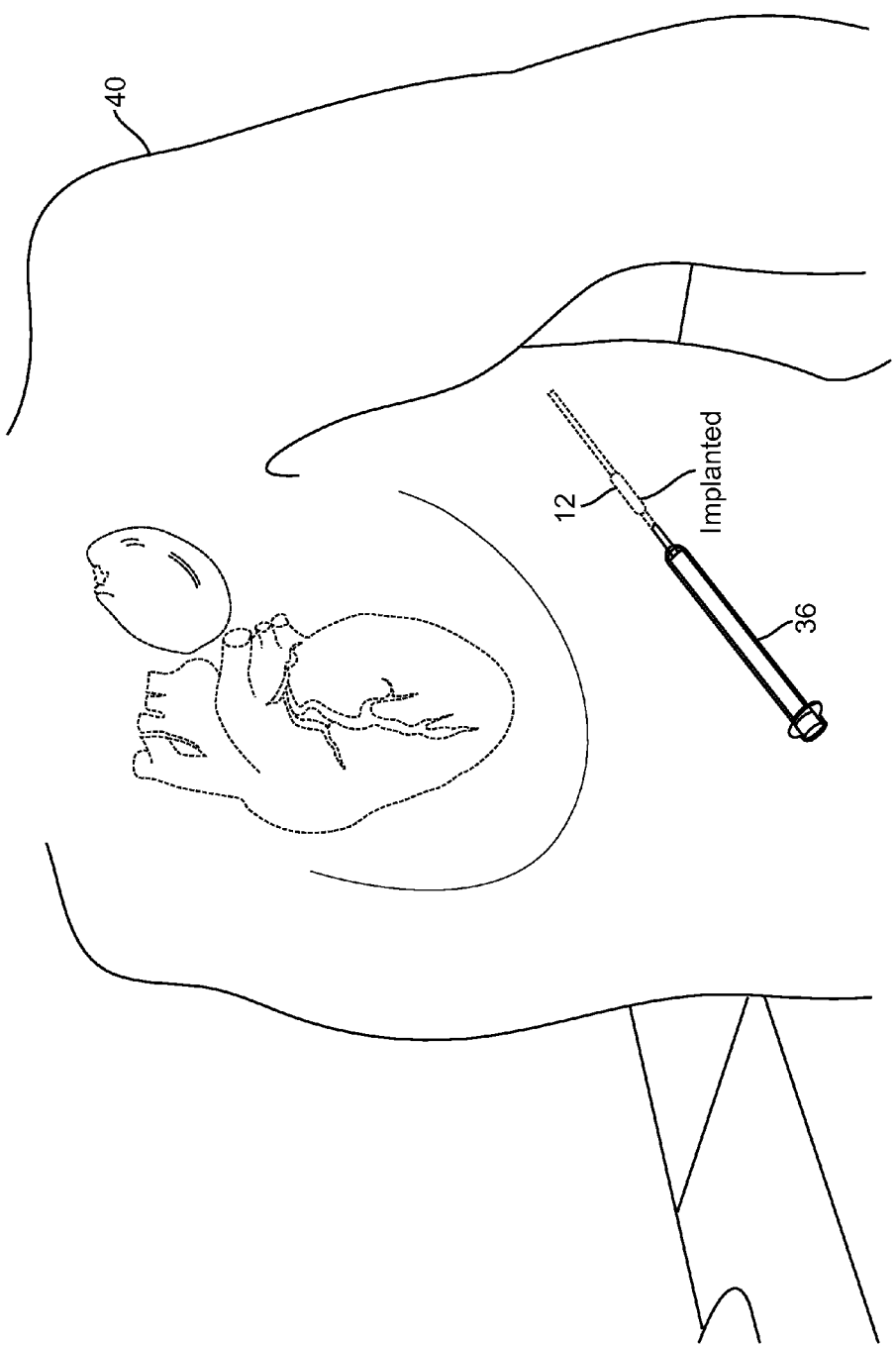
FIG. 2(d) illustrates the implanted sensor device of FIG. 2(a).
Figure 2E:
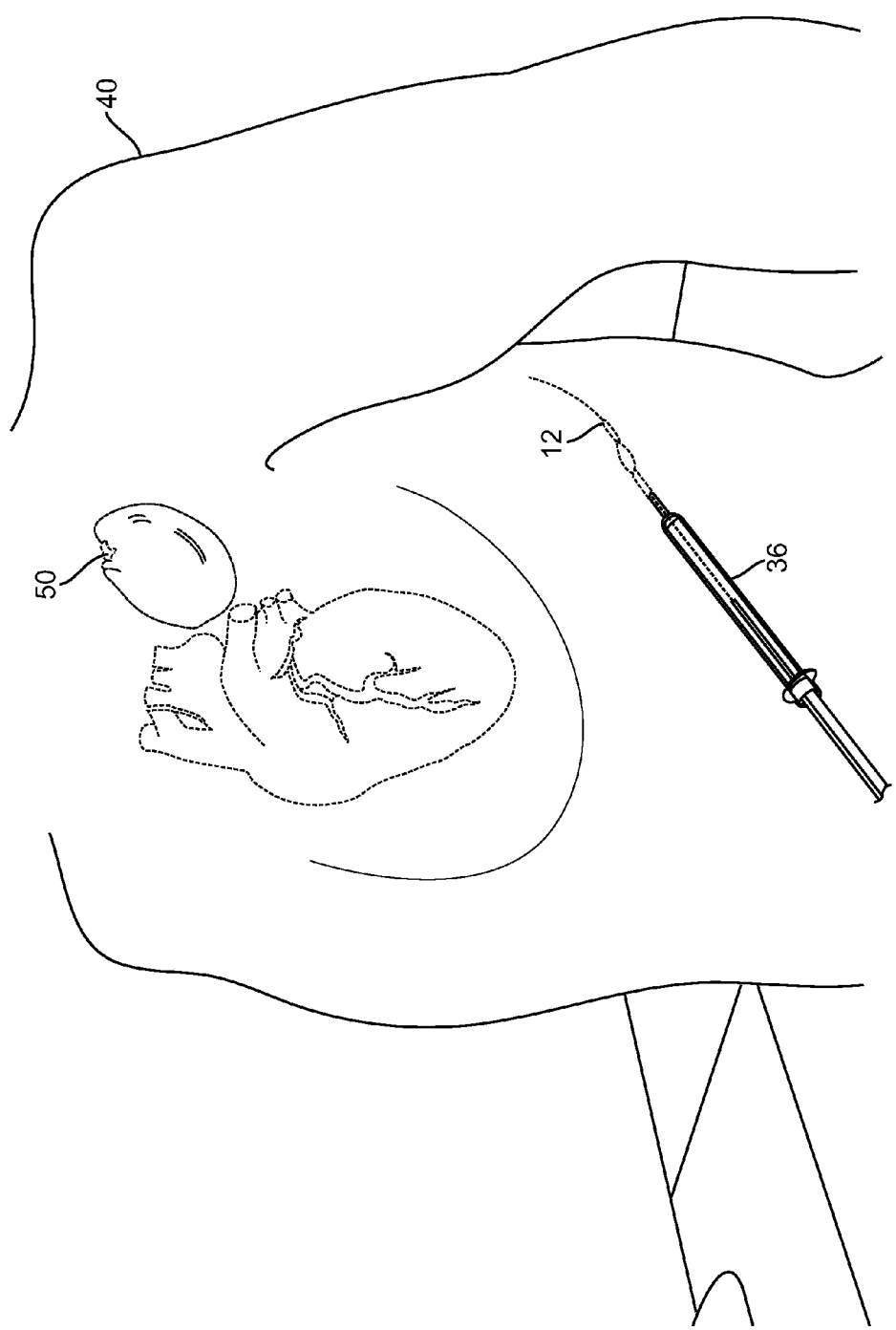
FIG. 2(e) illustrates the implanted sensor device of FIG. 2(a) as it flexes from a rigid state in the body.

FIG. 2(a) shows one embodiment of the injectable detecting system 12 with sensors 14 that is introduced below the skin surface. The sensor device includes power and communication elements 32, and a communication antenna 34. The antenna may be a self expanding antenna expandable from a first compressed shape to a second expanded shape, such as disclosed in U.S. Provisional Application No. 61/084,567, filed Jul. 29, 2008 entitled "Communication-Anchor Loop For Injectable Device", the full disclosure of which is incorporated herein by reference. FIG. 2(b) illustrates the injectable detecting system 12 being loaded into an injector 36 having a needle end 38. FIG. 2(c) shows the injectable detecting system 12 being introduced subcutaneously into a patient 40. FIG. 2(d) shows the injectable detecting system 12 being implanted subcutaneously from the injector 36. In FIG. 2(e), the injector 36 is removed and the injectable detecting system 12 flexes from a rigid configuration.

Figure 2F:
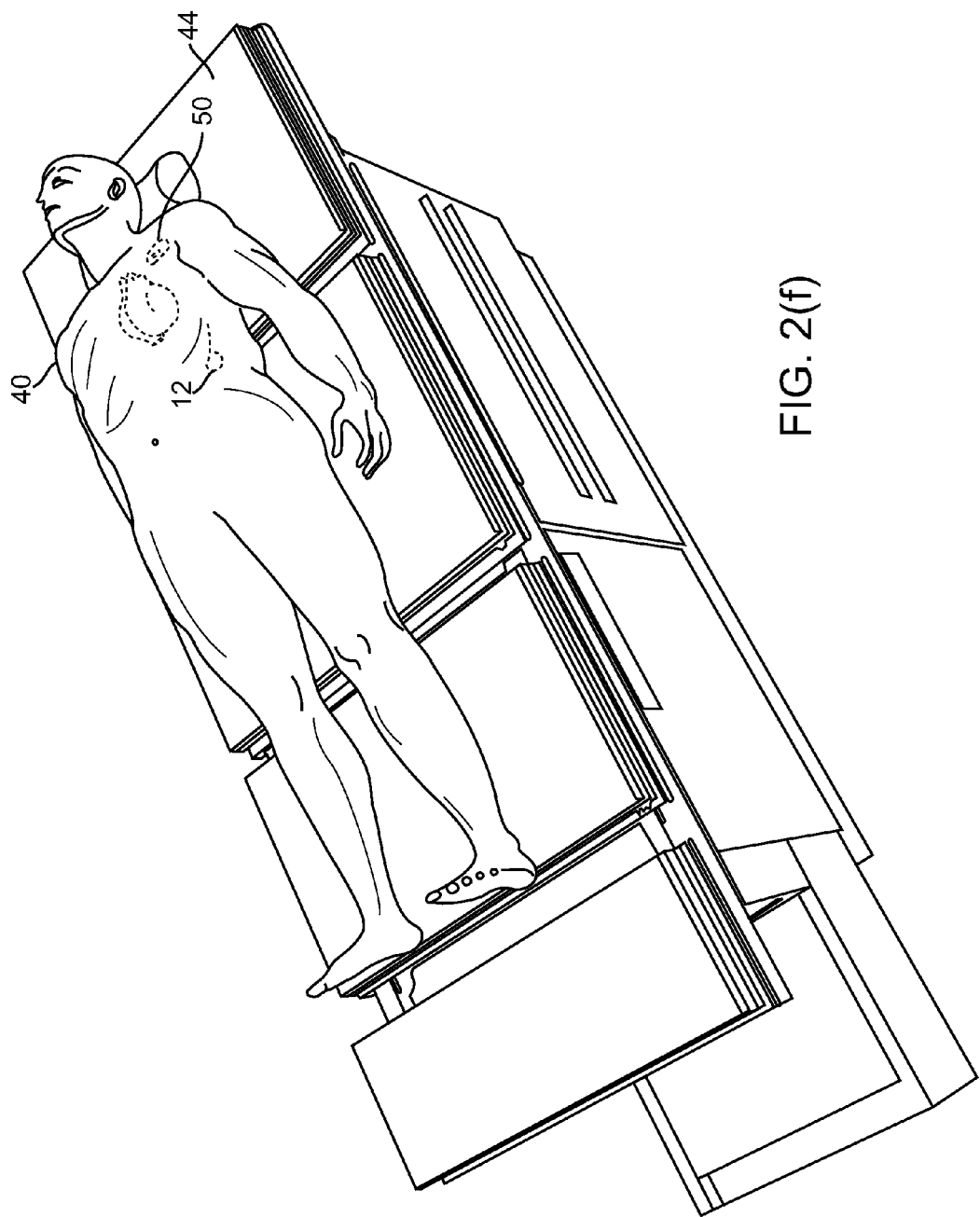
FIG. 2(f) illustrates a patient laying on top of a matt that has coils, where downloading of patient data and recharging can occur via the matt.
Figure 2G:
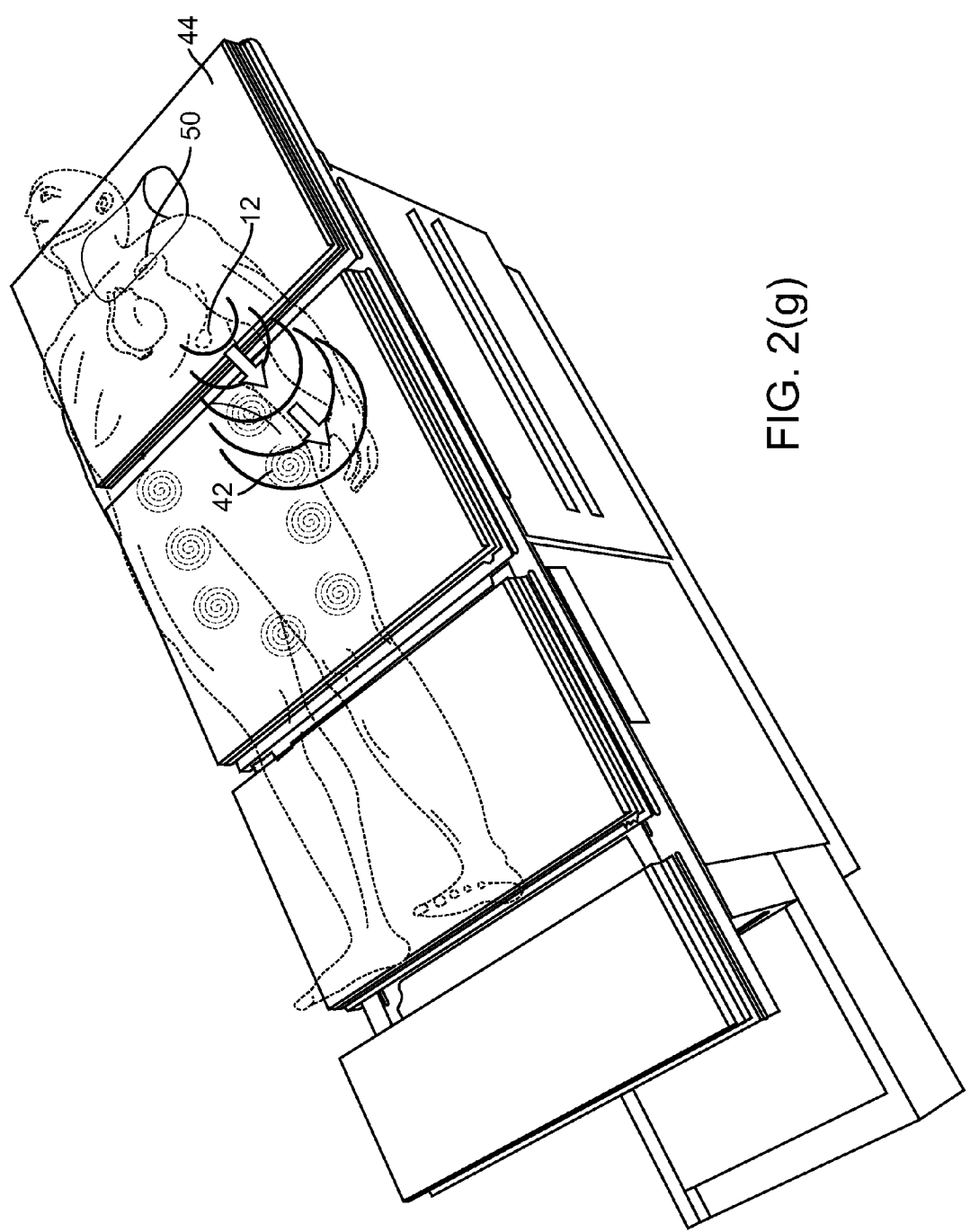
FIG. 2(g) illustrates the patient laying on top of the matt from FIG. 2(f) and the downloading of data from the sensors to the matt.
Figure 2H:
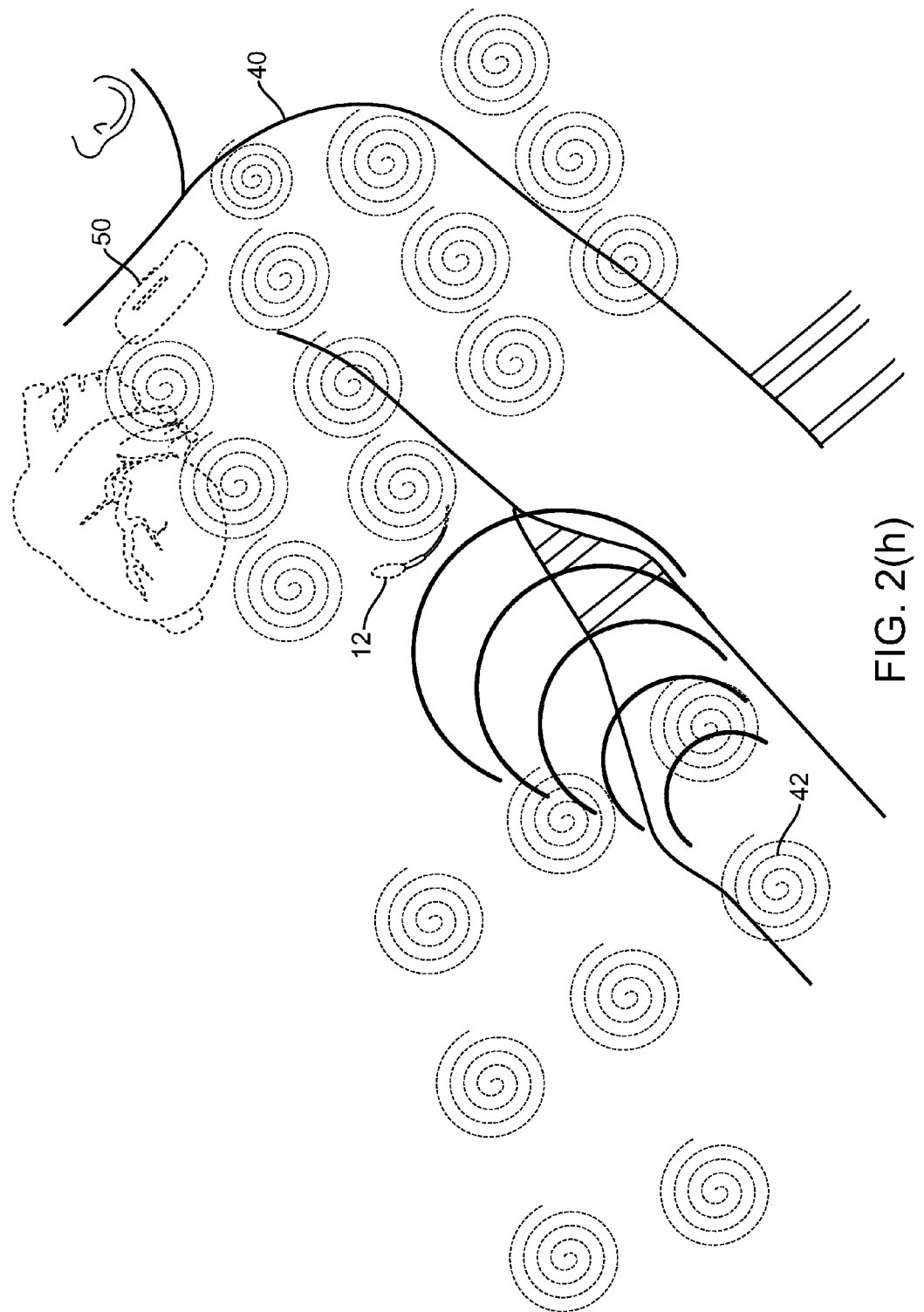
FIG. 2(h) is a close up view of FIG. 2(g), showing the downloading of data from the sensors to the matt, and then transfer of the data from the matt to a modem.
Figure 2I:
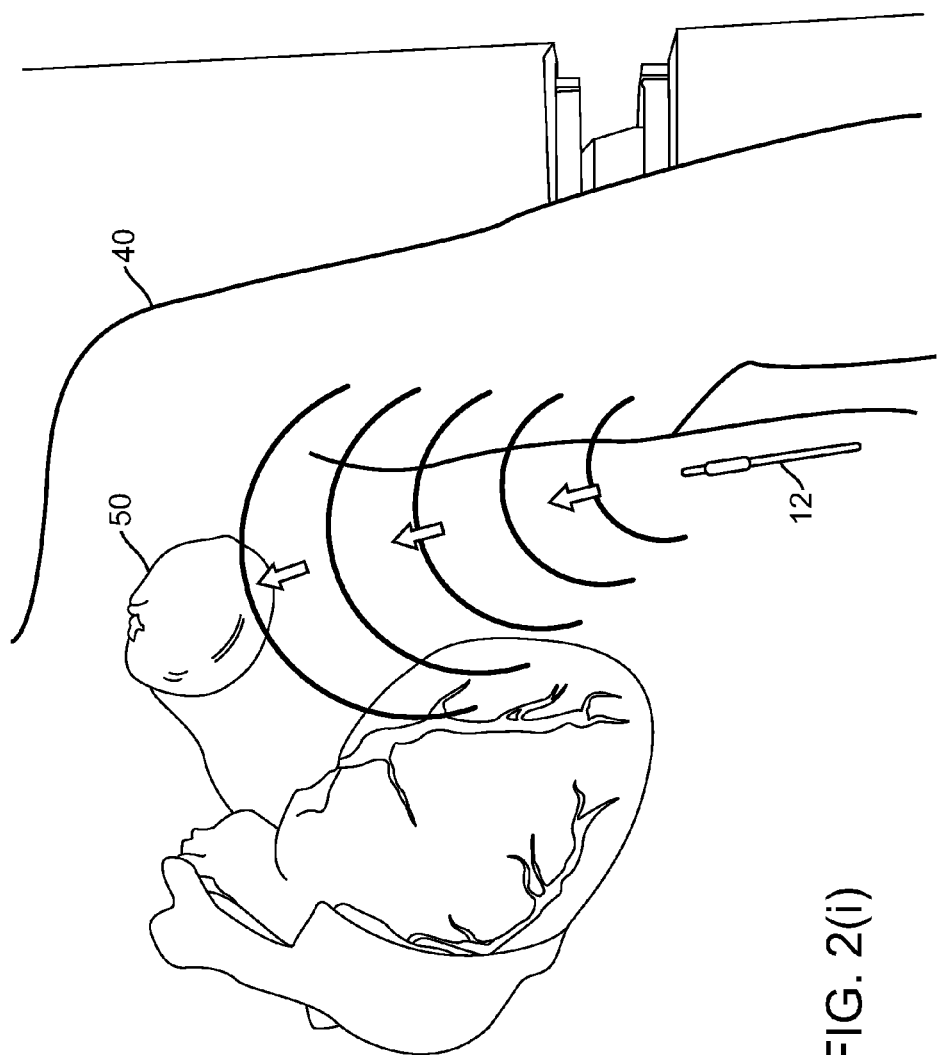
FIG. 2(i) illustrates a patient with an implanted device, such as a pacing device, and the implanted device of FIG. 2(a) in communication with the implanted device.

In one embodiment, illustrated in FIGS. 2(f) and 2(g), recharging coils 42 are placed in a mat 44 on the patient's bed, such as under a mattress pad. Recharging of the sensors/battery and data transfer can occur during sleep of the patient. The rechargeable batteries can be transcutaneously charged with an external unit other than the mat. FIG. 2(g) shows downloading from the sensors and data transfer during sleep of the patient. In FIG. 2(h), the sensors download data to the mat and a modem is used from data transfer. In FIG. 2(I), an implantable device 50, such as a pacing device communicates with the injectable detecting system 12 of FIG. 2(a).

In one embodiment, the wireless communication device 16 is configured to receive instructional data from the remote monitoring system and communicate instructions to the injectable detecting system.

Figure 3:
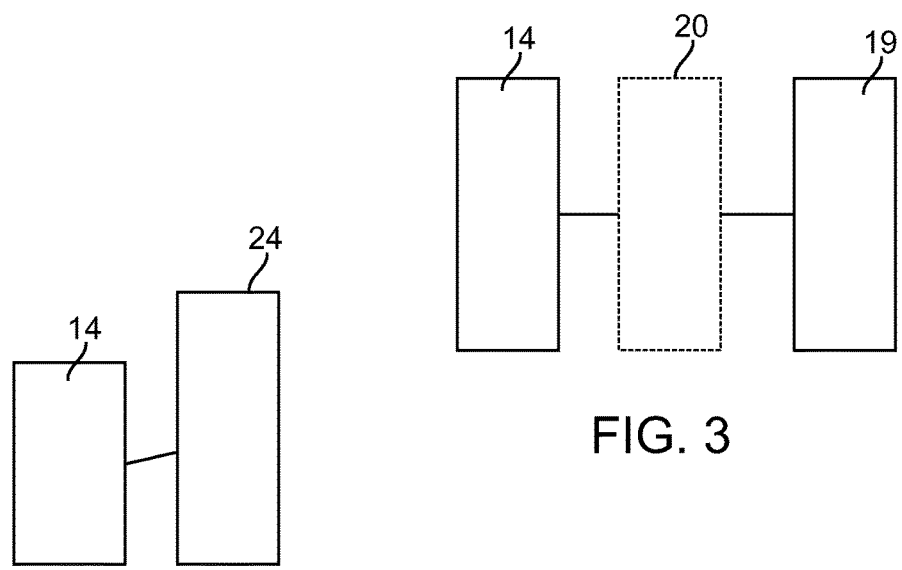
FIG. 3 illustrates one embodiment of an energy management device that is coupled to the plurality of sensors of FIG. 1.

As illustrated in FIG. 3, an energy management device 19 is coupled to the plurality of sensors. In one embodiment, the energy management device 19 is part of the detecting system. In various embodiments, the energy management device 19 performs one or more of, modulate drive levels per sensed signal of a sensor 14, modulate a clock speed to optimize energy, watch cell voltage drop—unload cell, coulomb-meter or other battery monitor, sensor dropoff at an end of life of a battery coupled to a sensor, battery end of life dropoff to transfer data, elective replacement indicator, call center notification, sensing windows by the sensors 14 based on a monitored physiological parameter and sensing rate control.

In one embodiment, the energy management device 19 is configured to manage energy by at least one of, a thermoelectric unit, kinetics, fuel cell, nuclear power, a micro-battery and with a rechargeable device.

The system 10 is configured to automatically detect events. The system 10 automatically detects events by at least one of, high noise states, physiological quietness, sensor continuity and compliance. In response to a detected physiological event, patient states are identified when data collection is inappropriate. In response to a detected physiological event, patient states are identified when data collection is desirable. Patient states include, physiological quietness, rest, relaxation, agitation, movement, lack of movement and a patient's higher level of patient activity.

The system uses an intelligent combination of sensors to enhance detection and prediction capabilities, as more fully discloses in U.S. patent application Ser. Nos. 60/972,537 filed Sep. 14, 2008 and 61/055,666 filed May 23, 2008, both titled "Adherent Device with Multiple Physiological Sensors", incorporated herein by reference, and as more fully explained below.

In one embodiment, the injectable detecting system 12 communicates with the remote monitoring system 18 periodically or in response to a trigger event. The trigger event can include but is not limited to at least one of, time of day, if a memory is full, if an action is patient initiated, if an action is initiated from the remote monitoring system, a diagnostic event of the monitoring system, an alarm trigger, a mechanical trigger, and the like.

The injectable detecting system 12 can continuously, or non-continuously, monitor the patient, alerts are provided as necessary and medical intervention is provided when required. In one embodiment, the wireless communication device 16 is a wireless local area network for receiving data from the plurality of sensors in the injectable detecting system.

A processor 20 is coupled to the plurality of sensors 14 in the injectable detecting system 12. The processor 20 receives data from the plurality of sensors 14 and creates processed patient data. In one embodiment, the processor 20 is at the remote monitoring system 18. In another embodiment, the processor 20 is at the detecting system 12. The processor 20 can be integral with a monitoring unit 22 that is part of the injectable detecting system 12 or part of the remote monitoring system 18.

The processor 20 has program instructions for evaluating values received from the sensors 14 with respect to acceptable physiological ranges for each value received by the processor 20 and determine variances. The processor 20 can receive and store a sensed measured parameter from the sensors 14, compare the sensed measured value with a predetermined target value, determine a variance, accept and store a new predetermined target value and also store a series of questions from the remote monitoring system 18.

Figure 4:
FIG. 4 illustrates one embodiment of present invention illustrating logic resources configured to receive data from the sensors and/or the processed patient for monitoring purposes, analysis and/or prediction purposes.

As illustrated in FIG. 4, logic resources 24 are provided that take the data from the sensors 14, and/or the processed patient data from the processor 20, to predict an impending decompensation. The logic resources 24 can be at the remote monitoring system 18 or at the detecting system 12, such as in the monitoring unit 22.

Figure 5:
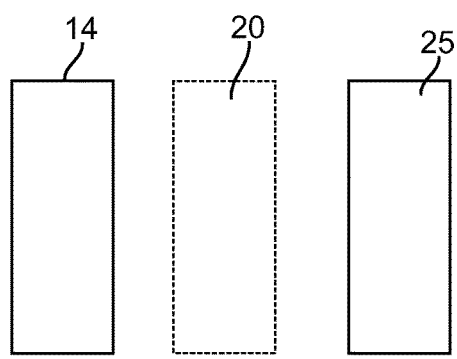
FIG. 5 illustrates an embodiment of the patient monitoring system of the present invention with a memory management device.

In one embodiment, a memory management device 25 is provided as illustrated in FIG. 5. In various embodiments, the memory management device 25 performs one or more of data compression, prioritizing of sensing by a sensor 14, monitoring all or some of sensor data by all or a portion of the sensors 14, sensing by the sensors 14 in real time, noise blanking to provide that sensor data is not stored if a selected noise level is determined, low-power of battery caching and decimation of old sensor data.

The injectable detecting system 12 can provide a variety of different functions, including but not limited to, initiation, programming, measuring, storing, analyzing, communicating, predicting, and displaying of a physiological event of the patient. The injectable detecting system 12 can be sealed, such as housed in a hermetically sealed package. In one embodiment, at least a portion of the sealed packages include a power source, a memory, logic resources and a wireless communication device. In one embodiment, an antenna is included that is exterior to the sealed package of the injectable detecting system 12. In one embodiment, the sensors 14 include, flex circuits, thin film resistors, organic transistors and the like. The sensors 14 can include ceramics, titanium PEEK, along with a silicon, PU or other insulative adherent sealant, to enclose the electronics. Additionally, all or part of the injectable detecting system 12 can include drug eluting coatings, including but not limited to, an antibiotic, anti-inflammatory agent and the like.

A wide variety of different sensors 14 can be utilized, including but not limited to, bioimpedance, heart rate, heart rhythm, HRV, HRT, heart sounds, respiration rate, respiration rate variability, respiratory sounds, $SpO_2$, blood pressure, activity, posture, wake/sleep, orthopnea, temperature, heat flux, an accelerometer, glucose sensor, other chemical sensors associated with cardiac conditions, and the like. A variety activity sensors can be utilized, including but not limited to a, ball switch, accelerometer, minute ventilation, HR, bioimpedance noise, skin temperature/heat flux, BP, muscle noise, posture and the like.

The output of the sensors 14 can have multiple features to enhance physiological sensing performance. These multiple features have multiple sensing vectors that can include redundant vectors. The sensors 14 can include current delivery electrodes and sensing electrodes. Size and shape of current delivery electrodes, and the sensing electrodes, can be optimized to maximize sensing performance. The system 10 can be configured to determine an optimal sensing configuration and electronically reposition at least a portion of a sensing vector of a sensing electrode. The multiple features enhance the system's 10 ability to determine an optimal sensing configuration and electronically reposition sensing vectors. In one embodiment, the sensors 14 can be partially masked to minimize contamination of parameters sensed by the sensors 14.

The size and shape of current delivery electrodes, for bioimpedance, and sensing electrodes can be optimized to maximize sensing performance Additionally, the outputs of the sensors 14 can be used to calculate and monitor blended indices. Examples of the blended indices include but are not limited to, heart rate (HR) or respiratory rate (RR) response to activity, HR/RR response to posture change, HR+RR, HR/RR+bioimpedance, and/or minute ventilation/accelerometer and the like.

The sensors 14 can be cycled in order to manage energy, and different sensors 14 can sample at different times. By way of illustration, and without limitation, instead of each sensor 14 being sampled at a physiologically relevant interval, e.g. every 30 seconds, one sensor 14 can be sampled at each interval, and sampling cycles between available sensors.

By way of illustration, and without limitation, the sensors 14 can sample 5 seconds for every minute for ECG, once a second for an accelerometer sensor, and 10 seconds for every 5 minutes for impedance.

In one embodiment, a first sensor 14 is a core sensor 14 that continuously monitors and detects, and a second sensor 14 verifies a physiological status in response to the core sensor 14 raising a flag. Additionally, some sensors 14 can be used for short term tracking, and other sensors 14 used for long term tracking.

The injectable detecting system 12 is inserted into the patient by a variety of means, including but not limited to, catheter delivery, blunt tunneling, insertion with a needle, by injection, with a gun or syringe device with a stiffening wire and stylet and the like. The sensors 14 can be inserted in the patient in a non-sterile or sterile setting, non-surgical setting or surgical setting, injected with our without anesthesia and injected with or without imaging assistance. The injectable detecting system 12 can be anchored in the patient by a variety of means including but not limited to, barbs, anchors, tissue adhesion pads, suture loops.

The injectable detecting system 12 can come in a variety of different form factors including but not limited to, cylinder, dog-bone, half dog-bone, trapezoidal cross-section, semicircular cross-section, star-shaped cross-section, v-shaped cross-section, L-shaped, canted, W shaped, or in other shapes that assist in their percutaneous delivery, S-shaped, sine-wave shaped, J-shaped, any polygonal shape, helical/spiral, fin electrodes, and linear device with a radius of curvature to match a radius of the injection site and the like. Further, the injectable detecting system 12 can have flexible body configurations. Additionally, the injectable detecting system 12 can be configured to deactivate selected sensors 14 to reduce redundancy.

The sensors 14 can be made of a variety of materials, including but not limited to, silicone, polyurethane, Nitinol, a biocompatible material, a bioabsorbable material and the like. Electrode sensors 14 can have a variety of different conductors, including but not limited to, platinum, MP35N which is a nickel-cobalt-chromium-molybdenum alloy, MP35N/Ag core, platinum/tantalum core, stainless steel, titanium and the like. The sensors 14 can have insulative materials, including but not limited to, polyetheretherketone (PEEK), ethylene-tetrafluoroethylene (ETFE), polytetra-fluoroethylene (PTFE), polyimide, silicon, polyurethane, and the like. Further, the sensors 14 can have openings, or an absorbent material, configured to sample a hydration level or electrolyte level in a surrounding tissue site at the location of the sensor 14. The sensor 14 electrodes can be made of a variety of materials, including but not limited to platinum, iridium, titanium, and the like. Electrode coatings can be included, such as iridium oxide, platinum black, TiN, and the like.

The injectable detecting system 12 can include one or more a rechargeable batteries 36 that can be transcutaneously chargeable with an external unit.

Figure 6:
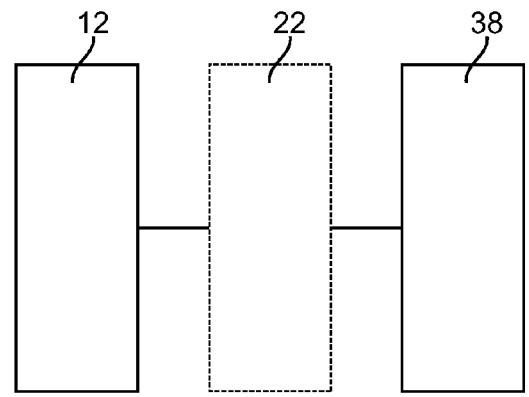
FIG. 6 illustrates an embodiment of the patient monitoring system of the present invention with an external device coupled to the sensors.

Referring to FIG. 6, in one embodiment, an external device 38, including a medical treatment device, is coupled to the injectable detecting system 12. The external device 38 can be coupled to a monitoring unit 22 that is part of the injectable detecting system 12, or in direct communication with the sensors 14. A variety of different external devices 38 can be used, including but not limited to, a weight scale, blood pressure cuff, cardiac rhythm management device, a medical treatment device, medicament dispenser, glucose monitor, insulin pump, drug delivery pumps, drug delivery patches, and the like. Suitable cardiac rhythm management devices include but are not limited to, Boston Scientific's Latitude system, Medtronic's CareLink system, St. Jude Medical's HouseCall system and the like. Such communication may occur directly or via an external translator unit.

The external device 38 can be coupled to an auxiliary input of the monitoring unit 22 at the injectable detecting system 12 or to the monitoring system 22 at the remote monitoring system 18. Additionally, an automated reader can be coupled to an auxiliary input in order to allow a single monitoring unit 22 to be used by multiple patients. As previously mentioned above, the monitoring unit 22 can be at the remote monitoring system 18 and each patient can have a patient identifier (ID) including a distinct patient identifier. In addition, the ID identifier can also contain patient specific configuration parameters. The automated reader can scan the patient identifier ID and transmit the patient ID number with a patient data packet such that the main data collection station can identify the patient.

It will be appreciated that other medical treatment devices can also be used. The injectable detecting system 12 can communicate wirelessly with the external devices 38 in a variety of ways including but not limited to, a public or proprietary communication standard and the like. The injectable detecting system 12 can be configured to serve as a communication hub for multiple medical devices, coordinating sensor data and therapy delivery while transmitting and receiving data from the remote monitoring system 18.

In one embodiment, the injectable detecting system 12 coordinate data sharing between the external systems 38 allowing for sensor integration across devices. The coordination of the injectable detecting system 12 provides for new pacing, sensing, defibrillation vectors, and the like.

In one embodiment, the processor 20 is included in the monitoring unit 22 and the external device 38 is in direct communication with the monitoring unit 22.

Figure 7:
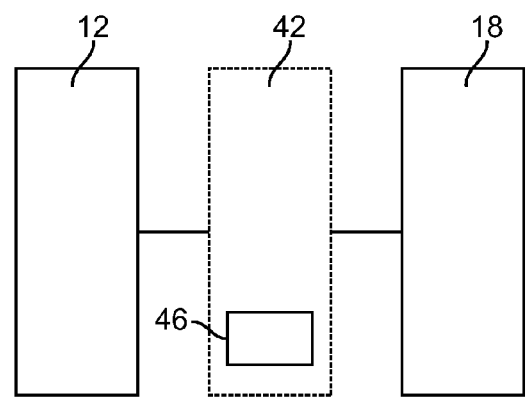
FIG. 7 illustrates an embodiment of the patient monitoring system of the present invention with a notification device.

In another embodiment, illustrated in FIG. 7, a notification device 42 is coupled to the injectable detecting system 12 and the remote monitoring system 18. The notification device 42 is configured to provide notification when values received from the sensors 14 are not within acceptable physiological ranges. The notification device 42 can be at the remote monitoring system 18 or at the monitoring unit 22 that is part of the injectable detecting system 12. A variety of notification devices 42 can be utilized, including but not limited to, a visible patient indicator, an audible alarm, an emergency medical service notification, a call center alert, direct medical provider notification and the like. The notification device 42 provides notification to a variety of different entities, including but not limited to, the patient, a caregiver, the remote monitoring system, a spouse, a family member, a medical provider, from one device to another device such as the external device 38, and the like.

Notification can be according to a preset hierarchy. By way of illustration, and without limitation, the preset hierarchy can be, patient notification first and medical provider second, patient notification second and medical provider first, and the like. Upon receipt of a notification, a medical provider, the remote monitoring system 18, or a medical treatment device can trigger a high-rate sampling of physiological parameters for alert verification.

The system 10 can also include an alarm 46, that can be coupled to the notification device 42, for generating a human perceptible signal when values received from the sensors 14 are not within acceptable physiological ranges. The alarm 46 can trigger an event to render medical assistance to the patient, provide notification as set forth above, continue to monitor, wait and see, and the like.

When the values received from the sensors 14 are not within acceptable physiological ranges the notification is with the at least one of, the patient, a spouse, a family member, a caregiver, a medical provider and from one device to another device, to allow for therapeutic intervention to prevent decompensation.

In another embodiment, the injectable detecting system 12 can switch between different modes, wherein the modes are selected from at least one of, a stand alone mode with communication directly with the remote monitoring system 18, communication with an implanted device, communication with a single implanted device, coordination between different devices (external systems) coupled to the plurality of sensors and different device communication protocols.

By way of illustration, and without limitation, the patient can be a congestive heart failure patient. Heart failure status is determined by a weighted combination change in sensor outputs and be determined by a number of different means, including but not limited to, (i) when a rate of change of at least two sensor outputs is an abrupt change in the sensor outputs as compared to a change in the sensor outputs over a longer period of time, (ii) by a tiered combination of at least a first and a second sensor output, with the first sensor output indicating a problem that is then verified by at least a second sensor output, (iii) by a variance from a baseline value of sensor outputs, and the like. The baseline values can be defined in a look up table.

In another embodiment, heart failure status is determined using three or more sensors by at least one of, (i) when the first sensor output is at a value that is sufficiently different from a baseline value, and at least one of the second and third sensor outputs is at a value also sufficiently different from a baseline value to indicate heart failure status, (ii) by time weighting the outputs of the first, second and third sensors, and the time weighting indicates a recent event that is indicative of the heart failure status and the like.

In one embodiment, the wireless communication device 16 can include a, modem, a controller to control data supplied by the injectable detecting system 12, serial interface, LAN or equivalent network connection and a wireless transmitter. Additionally, the wireless communication device 16 can include a receiver and a transmitter for receiving data indicating the values of the physiological event detected by the plurality of sensors, and for communicating the data to the remote monitoring system 18. Further, the wireless communication device 16 can have data storage for recording the data received from the injectable detecting system 12 and an access device for enabling access to information recording in the data storage from the remote monitoring system 18.

In various embodiments, the remote monitoring system 18 can include a, receiver, a transmitter and a display for displaying data representative of values of the one physiological event detected by the injectable detecting system 12. The remote monitoring system can also include a, data storage mechanism that has acceptable ranges for physiological values stored therein, a comparator for comparing the data received from the injectable detecting system 12 with the acceptable ranges stored in the data storage device and a portable computer. The remote monitoring system 18 can be a portable unit with a display screen and a data entry device for communicating with the wireless communication device 16.

Figure 8:
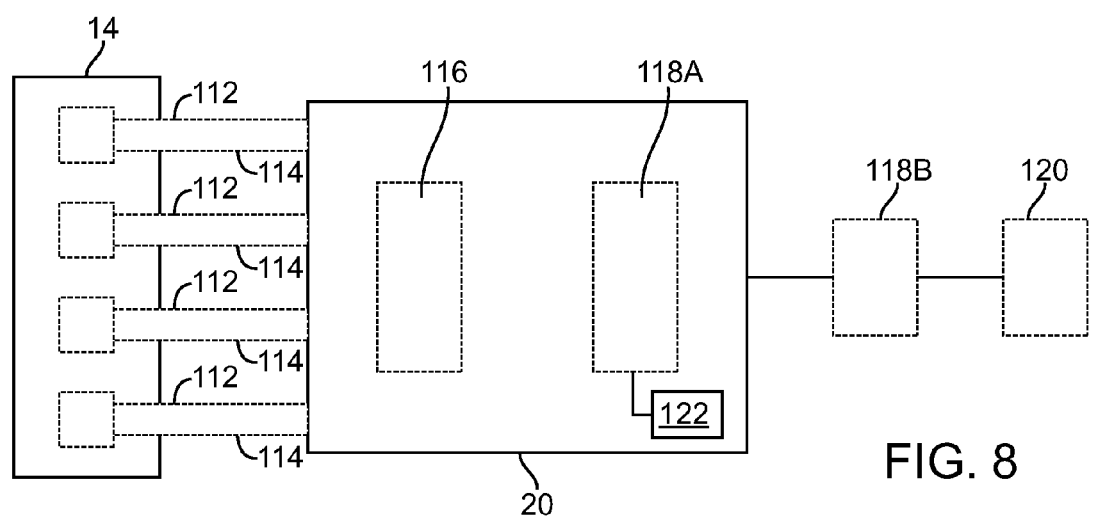
FIG. 8 is a block diagram illustrating an embodiment of the present invention with sensor leads that convey signals from the sensors to a monitoring unit at the detecting system, or through a wireless communication device to a remote monitoring system.

Referring now to FIG. 8, for each sensor 14, a sensor lead 112 and 114 conveys signals from the sensor 14 to the monitoring unit 22 at the injectable detecting system 12, or through the wireless communication device 16 to the remote monitoring system 18.

In one embodiment, each signal from a sensor 14 is first passed through a low-pass filter 116, at the injectable detecting system 12 or at the remote monitoring system 18, to smooth the signal and reduce noise. The signal is then transmitted to an analog-to-digital converter 118A, which transforms the signals into a stream of digital data values that can be stored in a digital memory 118B. From the digital memory 118B, data values are transmitted to a data bus 120, along which they are transmitted to other components of the circuitry to be processed and archived. From the data bus 120, the digital data can be stored in a non-volatile data archive memory. The digital data can be transferred via the data bus 120 to the processor 20, which processes the data based in part on algorithms and other data stored in a non-volatile program memory.

The injectable detecting system 12 can also include a power management module 122 configured to power down certain components of the system, including but not limited to, the analog-to-digital converters 118A and 124, digital memories 118B and the non-volatile data archive memory and the like, between times when these components are in use. This helps to conserve battery power and thereby extend the useful life. Other circuitry and signaling modes may be devised by one skilled in the art.

Figure 9:
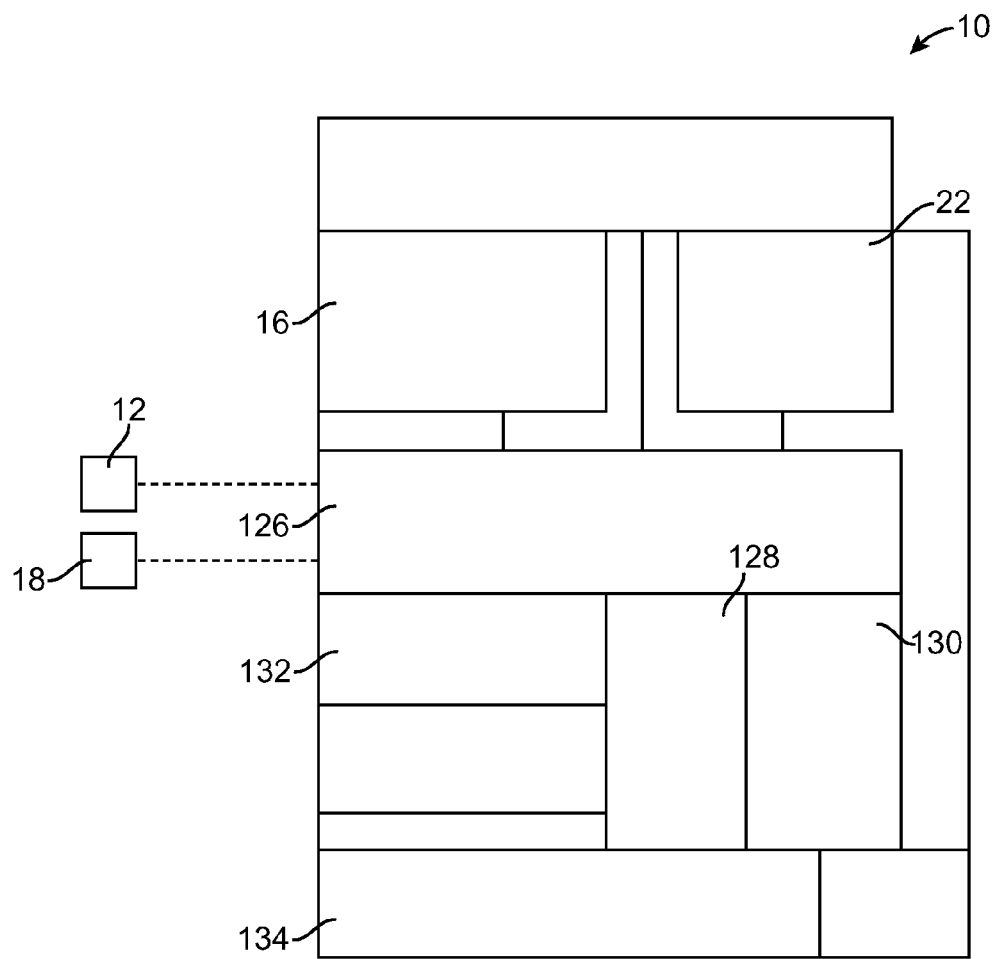
FIG. 9 is a block diagram illustrating an embodiment of the present invention with a control unit at the detecting system and/or the remote monitoring system.

As can be seen in FIG. 9, a control unit 126 is included at the detecting system 12, the remote monitoring system 18, or at both locations.

In one embodiment, the control unit 126 can be a microprocessor, for example, a Pentium or 486 processor. The control unit 126 can be coupled to the sensors 14 directly at the injectable detecting system 12, indirectly at the injectable detecting system 12 or indirectly at the remote monitoring system 18. Additionally the control unit 126 can be coupled to one or more devices, for example, a blood pressure monitor, cardiac rhythm management device, scale, a device that dispenses medication, a device that can indicate the medication has been dispensed, and the like.

Figure 10:
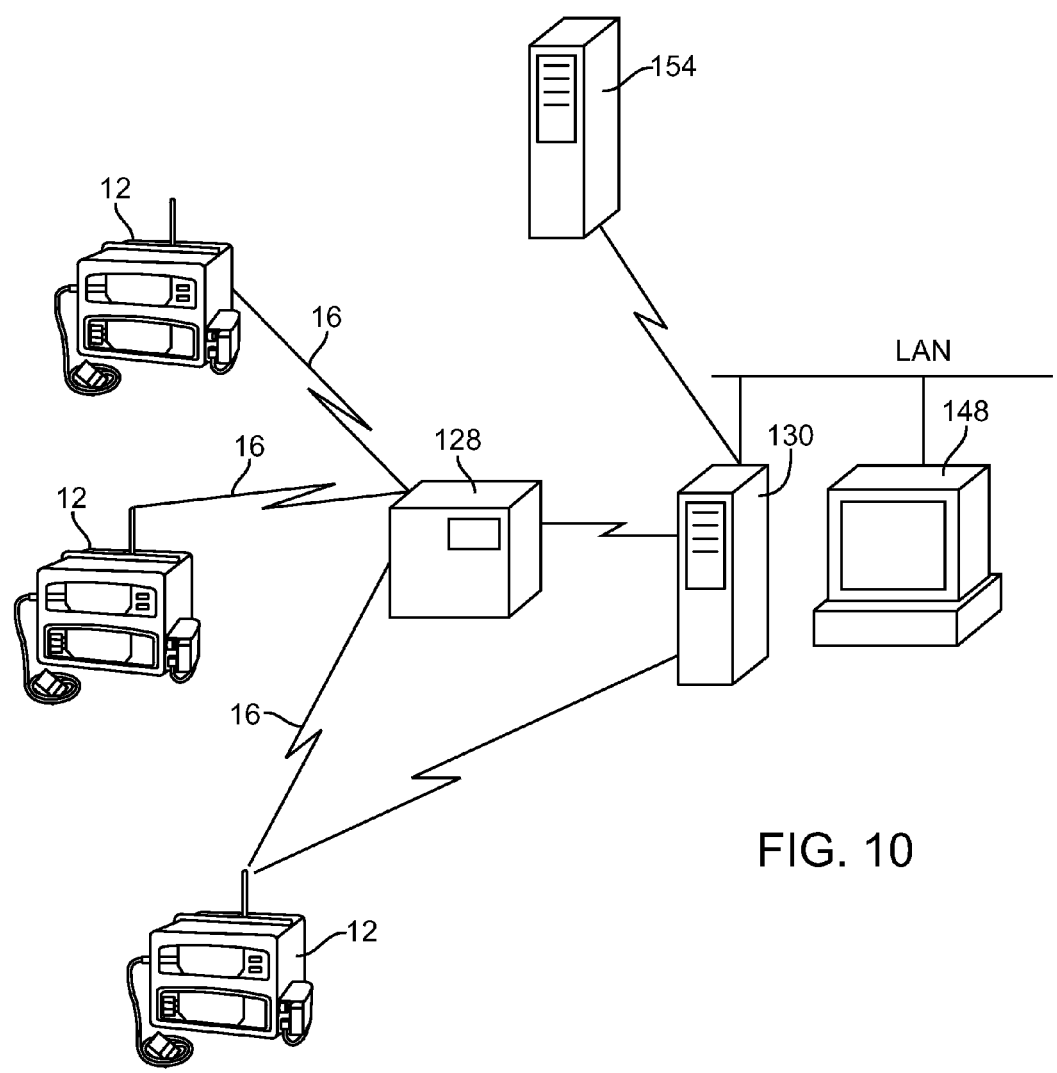
FIG. 10 is a block diagram illustrating an embodiment of the present invention where a control unit encodes patient data and transmits it to a wireless network storage unit at the remote monitoring system.

The control unit 126 can be powered by AC inputs which are coupled to internal AC/DC converters 134 that generate multiple DC voltage levels. After the control unit 126 has collected the patient data from the sensors 14, the control unit 126 encodes the recorded patient data and transmits the patient data through the wireless communication device 16 to transmit the encoded patient data to a wireless network storage unit 128 at the remote monitoring system 18, as shown in FIG. 10. In another embodiment, wireless communication device 16 transmits the patient data from the injectable detecting system 12 to the control unit 126 when it is at the remote monitoring system 18.

Every time the control unit 126 plans to transmit patient data to a main data collection station 130, located at the remote monitoring system 18, the control unit 126 attempts to establish a communication link. The communication link can be wireless, wired, or a combination of wireless and wired for redundancy, e.g., the wired link checks to see if a wireless communication can be established. If the wireless communication link 16 is available, the control unit 126 transmits the encoded patient data through the wireless communication device 16. However, if the wireless communication device 16 is not available for any reason, the control unit 126 waits and tries again until a link is established.

Figure 11:
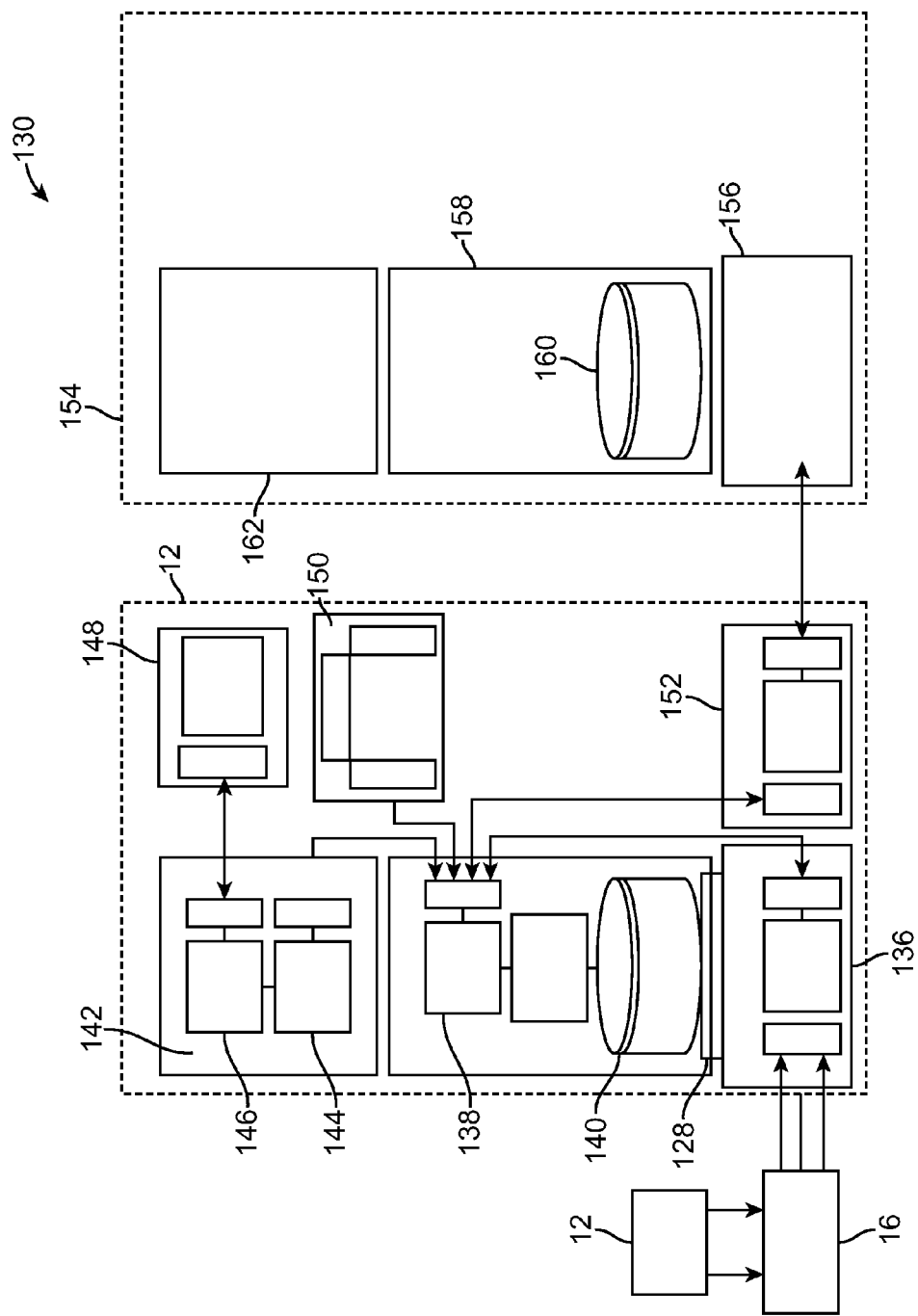
FIG. 11 is a block diagram illustrating one embodiment of an internal structure of a main data collection station at the remote monitoring system of the present invention.

Referring now to FIG. 11, one embodiment of an internal structure of a main data collection station 130, at the remote monitoring system 18, is illustrated. The patient data can be transmitted by the remote monitoring system 18 by either the wireless communication device 16 or conventional modem to the wireless network storage unit 128. After receiving the patient data, the wireless network storage unit 128 can be accessed by the main data collection station 130. The main data collection station 130 allows the remote monitoring system 18 to monitor the patient data of numerous patients from a centralized location without requiring the patient or a medical provider to physically interact with each other.

The main data collection station 130 can include a communications server 136 that communicates with the wireless network storage unit 128. The wireless network storage unit 128 can be a centralized computer server that includes a unique, password protected mailbox assigned to and accessible by the main data collection station 130. The main data collection station 130 contacts the wireless network storage unit 128 and downloads the patient data stored in a mailbox assigned to the main data collection station 130.

Once the communications server 136 has formed a link with the wireless network storage unit 128, and has downloaded the patient data, the patient data can be transferred to a database server 138. The database server 138 includes a patient database 140 that records and stores the patient data of the patients based upon identification included in the data packets sent by each of the monitoring units 22. For example, each data packet can include an identifier.

Each data packet transferred from the remote monitoring system 18 to the main data collection station 130 does not have to include any patient identifiable information. Instead, the data packet can include the serial number assigned to the specific injectable detecting system 12. The serial number associated with the detecting system 12 can then be correlated to a specific patient by using information stored on the patient database 138. In this manner, the data packets transferred through the wireless network storage unit 128 do not include any patient-specific identification. Therefore, if the data packets are intercepted or improperly routed, patient confidentiality can not be breached.

The database server 138 can be accessible by an application server 142. The application server 142 can include a data adapter 144 that formats the patient data information into a form that can be viewed over a conventional web-based connection. The transformed data from the data adapter 144 can be accessible by propriety application software through a web server 146 such that the data can be viewed by a workstation 148. The workstation 148 can be a conventional personal computer that can access the patient data using proprietary software applications through, for example, HTTP protocol, and the like.

The main data collection station further can include an escalation server 150 that communicates with the database server 138. The escalation server 150 monitors the patient data packets that are received by the database server 138 from the monitoring unit 22. Specifically, the escalation server 150 can periodically poll the database server 138 for unacknowledged patient data packets. The patient data packets are sent to the remote monitoring system 18 where the processing of patient data occurs. The remote monitoring system 18 communicates with a medical provider in the event that an alert is required. If data packets are not acknowledged by the remote monitoring system 18. The escalation server 150 can be programmed to automatically deliver alerts to a specific medical provider if an alarm message has not been acknowledged within a selected time period after receipt of the data packet.

The escalation server 150 can be configured to generate the notification message to different people by different modes of communication after different delay periods and during different time periods.

The main data collection station 130 can include a batch server 152 connected to the database server 138. The batch server 152 allows an administration server 154 to have access to the patient data stored in the patient database 140. The administration server 154 allows for centralized management of patient information and patient classifications.

The administration server 154 can include a batch server 156 that communicates with the batch server 152 and provides the downloaded data to a data warehouse server 158. The data warehouse server 158 can include a large database 160 that records and stores the patient data.

The administration server 154 can further include an application server 162 and a maintenance workstation 164 that allow personnel from an administrator to access and monitor the data stored in the database 160.

The data packet utilized in the transmission of the patient data can be a variable length ASCII character packet, or any generic data formats, in which the various patient data measurements are placed in a specific sequence with the specific readings separated by commas. The control unit 126 can convert the readings from each sensor 14 into a standardized sequence that forms part of the patient data packet. In this manner, the control unit 126 can be programmed to convert the patient data readings from the sensors 14 into a standardized data packet that can be interpreted and displayed by the main data collection station 130 at the remote monitoring system 18.

Figure 12:
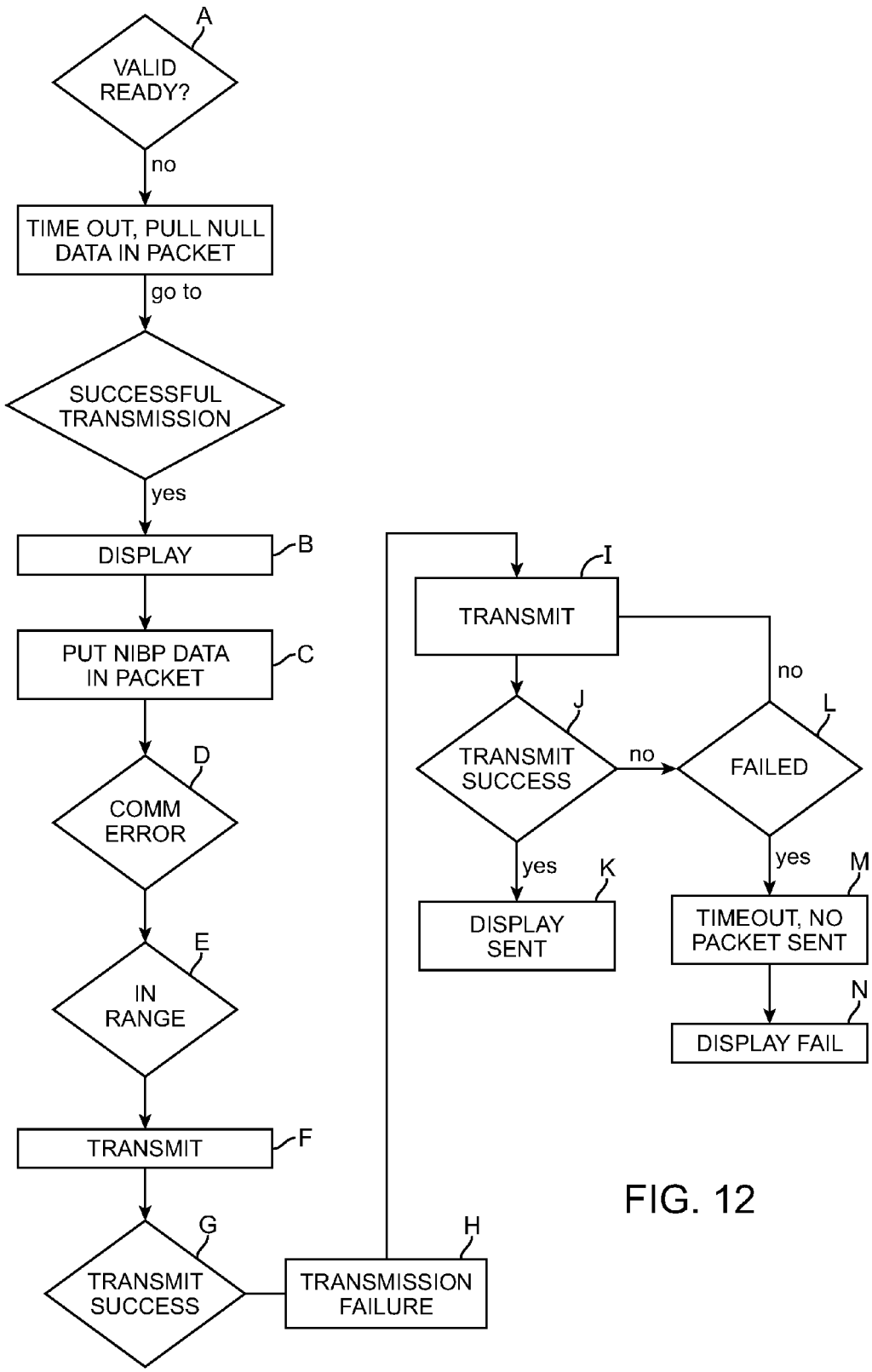
FIG. 12 is a flow chart illustrating an embodiment of the present invention with operation steps performed by the system of the present invention in transmitting information to the main data collection station.

Referring now to the flow chart of FIG. 12, if an external device 38 fails to generate a valid reading, as illustrated in step A, the control unit 126 fills the portion of the patient data packet associated with the external device 38 with a null indicator. The null indicator can be the lack of any characters between commas in the patient data packet. The lack of characters in the patient data packet can indicate that the patient was not available for the patient data recording. The null indicator in the patient data packet can be interpreted by the main data collection station 130 at the remote monitoring system 18 as a failed attempt to record the patient data due to the unavailability of the patient, a malfunction in one or more of the sensors 14, or a malfunction in one of the external devices 38. The null indicator received by the main data collection station 130 can indicate that the transmission from the injectable detecting system 12 to the remote monitoring system 18 was successful. In one embodiment, the integrity of the data packet received by the main data collection station 130 can be determined using a cyclic redundancy code, CRC-16, check sum algorithm. The check sum algorithm can be applied to the data when the message can be sent and then again to the received message.

After the patient data measurements are complete, the control unit 126 displays the sensor data, including but not limited to blood pressure cuff data and the like, as illustrated by step B. In addition to displaying this data, the patient data can be placed in the patient data packet, as illustrated in step C.

As previously described, the system 10 can take additional measurements utilizing one or more auxiliary or external devices 38 such as those mentioned previously. Since the patient data packet has a variable length, the auxiliary device patient information can be added to the patient data packet being compiled by the remote monitoring unit 22 during patient data acquisition period being described. Data from the external devices 38 is transmitted by the wireless communication device 16 to the remote monitoring system 18 and can be included in the patient data packet.

If the remote monitoring system 18 can be set in either the auto mode or the wireless only mode, the remote monitoring unit 22 can first determine if there can be an internal communication error, as illustrated in step D.

A no communication error can be noted as illustrated in step E. If a communication error is noted the control unit 126 can proceed to wireless communication device 16 or to a conventional modem transmission sequence, as will be described below. However, if the communication device is working, the control unit 126 can transmit the patient data information over the wireless network 16, as illustrated in step F. After the communication device has transmitted the data packet, the control unit 126 determines whether the transmission was successful, as illustrated in step G. If the transmission has been unsuccessful only once, the control unit 126 retries the transmission. However, if the communication device has failed twice, as illustrated in step H, the control unit 126 proceeds to the conventional modem process if the remote monitoring unit 22 was configured in an auto mode.

When the control unit 126 is at the injectable detecting system 12, and the control unit 126 transmits the patient data over the wireless communication device 16, as illustrated in step I, if the transmission has been successful, the display of the remote monitoring unit 22 can display a successful message, as illustrated in step J. However, if the control unit 126 determines in step K that the communication of patient data has failed, the control unit 126 repeats the transmission until the control unit 126 either successfully completes the transmission or determines that the transmission has failed a selected number of times, as illustrated in step L. The control unit 126 can time out the and a failure message can be displayed, as illustrated in steps M and N. Once the transmission sequence has either failed or successfully transmitted the data to the main data collection station, the control unit 126 returns to a start program step O.

As discussed previously, the patient data packets are first sent and stored in the wireless network storage unit 128. From there, the patient data packets are downloaded into the main data collection station 130. The main data collection station 130 decodes the encoded patient data packets and records the patient data in the patient database 140. The patient database 140 can be divided into individual storage locations for each patient such that the main data collection station 130 can store and compile patient data information from a plurality of individual patients.

A report on the patient's status can be accessed by a medical provider through a medical provider workstation that is coupled to the remote monitoring system 18. Unauthorized access to the patient database can be prevented by individual medical provider usernames and passwords to provide additional security for the patient's recorded patient data.

The main data collection station 130 and the series of work stations 148 allow the remote monitoring system 18 to monitor the daily patient data measurements taken by a plurality of patients reporting patient data to the single main data collection station 130. The main data collection station 130 can be configured to display multiple patients on the display of the workstations 148. The internal programming for the main data collection station 130 can operate such that the patients are placed in a sequential top-to-bottom order based upon whether or not the patient can be generating an alarm signal for one of the patient data being monitored. For example, if one of the patients monitored by monitoring system 130 has a blood pressure exceeding a predetermined maximum amount, this patient can be moved toward the top of the list of patients and the patient's name and/or patient data can be highlighted such that the medical personnel can quickly identify those patients who may be in need of medical assistance. By way of illustration, and without limitation, the following paragraphs is a representative order ranking method for determining the order which the monitored patients are displayed:

Alarm Display Order Patient Status Patients are then sorted 1 Medical Alarm Most alarms violated to least alarms violated, then oldest to newest 2 Missing Data Alarm Oldest to newest 3 Late Oldest to newest 4 Reviewed Medical Alarms Oldest to newest 5 Reviewed Missing Data Oldest to newest Alarms 6 Reviewed Null Oldest to newest 7 NDR Oldest to newest 8 Reviewed NDR Oldest to newest As listed in the above, the order of patients listed on the display can be ranked based upon the seriousness and number of alarms that are registered based upon the latest patient data information. For example, if the blood pressure of a single patient exceeds the tolerance level and the patient's heart rate also exceeds the maximum level, this patient will be placed above a patient who only has one alarm condition. In this manner, the medical provider can quickly determine which patient most urgently needs medical attention by simply identifying the patient's name at the top of the patient list. The order which the patients are displayed can be configurable by the remote monitoring system 18 depending on various preferences.

As discussed previously, the escalation server 150 automatically generates a notification message to a specified medical provider for unacknowledged data packets based on user specified parameters.

In addition to displaying the current patient data for the numerous patients being monitored, the software of the main data collection station 130 allows the medical provider to trend the patient data over a number of prior measurements in order to monitor the progress of a particular patient. In addition, the software allows the medical provider to determine whether or not a patient has been successful in recording their patient data as well as monitor the questions being asked by the remote monitoring unit 22.

As previously mentioned, the system 10 uses an intelligent combination of sensors to enhance detection and prediction capabilities. Electrocardiogram circuitry can be coupled to the sensors 14, or electrodes, to measure an electrocardiogram signal of the patient. An accelerometer can be mechanically coupled, for example adhered or affixed, to the sensors 14, adherent patch and the like, to generate an accelerometer signal in response to at least one of an activity or a position of the patient. The accelerometer signals improve patient diagnosis, and can be especially useful when used with other signals, such as electrocardiogram signals and impedance signals, including but not limited to, hydration respiration, and the like. Mechanically coupling the accelerometer to the sensors 14, electrodes, for measuring impedance, hydration and the like can improve the quality and/or usefulness of the impedance and/or electrocardiogram signals. By way of illustration, and without limitation, mechanical coupling of the accelerometer to the sensors 14, electrodes, and to the skin of the patient can improve the reliability, quality and/or accuracy of the accelerometer measurements, as the sensor 14, electrode, signals can indicate the quality of mechanical coupling of the patch to the patient so as to indicate that the device is connected to the patient and that the accelerometer signals are valid. Other examples of sensor interaction include but are not limited to, (i) orthopnea measurement where the breathing rate is correlated with posture during sleep, and detection of orthopnea, (ii) a blended activity sensor using the respiratory rate to exclude high activity levels caused by vibration (e.g. driving on a bumpy road) rather than exercise or extreme physical activity, (iii) sharing common power, logic and memory for sensors, electrodes, and the like.

While the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention.

What is claimed is:

1. An injectable device for use in physiological monitoring, comprising:
   a body having a shape configured for subcutaneous insertion in a patient;
   a plurality of sensors axially spaced along the body that provide an indication of at least one physiological event of the patient;
   a power source within the body;
   a communication antenna external to the body configured to transfer data to/from other devices, wherein the communication antenna is a self-expanding antenna having a compressed state prior to subcutaneous injection and expanded shape immediately after subcutaneous injection;
   a power and communication module within the body and coupled to the communication antenna and the plurality of sensors, wherein the power and communication module selectively supplies power to each of the plurality of sensors and receive sensor data from each of the plurality of sensors.

2. The injectable device of claim 1, wherein the body is flexible to allow conformance to adjacent tissue anatomy.

3. The injectable device of claim 1, wherein at least a portion of the body has a drug eluting coating.

4. The injectable device of claim 1, wherein the self-expanding communication antenna in the compressed state has a cross-sectional profile less than or equal to a cross-sectional profile of the body of the injectable device.

5. The injectable device of claim 1, wherein the power and communication module manages power consumption by the plurality of sensors.

6. The injectable device of claim 5, wherein the power and communication module manages power consumption of the plurality of sensors via at least one of modulating drive levels per sensor and modulating a clock speed.

7. The injectable device of claim 5, wherein the power and communication module manages power consumption by selectively sampling different types of sensors including in the plurality of sensors at different times.

8. The injectable device of claim 7, wherein the power and communication module continuously samples a first sensor, and monitors a second sensor in order to verify a physiological status flag raised by the first sensor.

9. The injectable device of claim 1, wherein the plurality of sensors includes two current delivery electrodes and two sensing electrodes for measuring bioimpedance.

10. The injectable device of claim 1, wherein at least one of the plurality of sensors has openings or an absorbent material configured to sample a hydration level or electrolyte level in a surrounding tissue site of the plurality of sensors.

11. The injectable device of claim 1, wherein the plurality of sensors further includes at least one activity sensor selected from at least one of, ball switch, accelerometer, minute ventilation, heart rate (HR), bioimpedance noise, skin temperature/heat flux, blood pressure (BP), muscle noise and posture.

12. The injectable device of claim 1, wherein the power source and the power and communication module are hermetically sealed, and wherein the communication antenna is external to the hermetically sealed portion.

13. The injectable device of claim 1, wherein the body and antenna are injectable in the patient by at least one of, catheter delivery, blunt tunneling, insertion with a needle, by injection, with a gun or syringe device with a stiffening wire stylet, guidewire, or combination of stylet or guidewire with a catheter.

14. An injectable system for physiological monitoring, the injectable system comprising:
   an injector having a first end configured to non-surgically puncture a patient's skin for subcutaneous insertion; and
   an injectable device having a rigid state that allows it to be housed within the injector and a flexible state assumed after subcutaneous insertion within the patient, wherein the injectable device includes a self-expanding communication antenna having a compressed state maintained by the injector while the injectable device is housed within the injector prior to subcutaneous injection and expanded shape after subcutaneous injection.

15. The injectable system of claim 14, wherein the injectable device includes:
   a flexible body having a shape configured for subcutaneous insertion in the patient;
   a plurality of sensors axially spaced along the flexible body that provide an indication of at least one physiological event of the patient;
   a power source within the flexible body;
   a power and communication module within the flexible body and coupled to the communication antenna and the plurality of sensors, wherein the power and communication module selectively supplies power to each of the plurality of sensors and receive sensor data from each of the plurality of sensors, wherein the self-expanding communication antenna is external to the flexible body.

16. The injectable system of claim 15, wherein at least a portion of the body has a drug eluting coating.

17. The injectable device of claim 14, wherein the body and antenna are injectable in the patient by at least one of, catheter delivery, blunt tunneling, insertion with a needle, by injection, with a gun or syringe device with a stiffening wire stylet, guidewire, or combination of stylet or guidewire with a catheter.

* * * * *